(12) United States Patent
Okazoe et al.

(10) Patent No.: US 6,956,138 B2
(45) Date of Patent: Oct. 18, 2005

(54) METHOD FOR PRODUCING A FLUORINE-CONTAINING COMPOUND

(75) Inventors: Takashi Okazoe, Yokohama (JP); Kunio Watanabe, Yokohama (JP); Shin Tatematsu, Yokohama (JP); Masahiro Ito, Yokohama (JP); Daisuke Shirakawa, Yokohama (JP); Masao Iwaya, Yokohama (JP); Hidekazu Okamoto, Yokohama (JP)

(73) Assignee: Asahi Glass Company, Limited, Tokyo (JP)

( * ) Notice: Subject to any disclaimer, the term of this patent is extended or adjusted under 35 U.S.C. 154(b) by 0 days.

(21) Appl. No.: 10/833,048

(22) Filed: Apr. 28, 2004

(65) Prior Publication Data

US 2004/0204618 A1 Oct. 14, 2004

Related U.S. Application Data

(62) Division of application No. 10/340,634, filed on Jan. 13, 2003, now Pat. No. 6,894,187, which is a continuation of application No. PCT/JP01/06024, filed on Jul. 11, 2001.

(30) Foreign Application Priority Data

| Jul. 11, 2000 | (JP) | ..................... | 2000-210184 |
| Sep. 27, 2000 | (JP) | ..................... | 2000-294994 |
| Apr. 5, 2001 | (JP) | ..................... | 2001-107560 |

(51) Int. Cl.$^{7}$ .................. C07C 43/30; C07C 53/38; C07C 51/58
(52) U.S. Cl. .................. 568/600; 568/604; 562/849; 562/852; 562/863
(58) Field of Search ............... 562/849, 852; 562/863; 568/600, 604

(56) References Cited

U.S. PATENT DOCUMENTS

| 3,900,372 | A | 8/1975 | Childs .................. 204/81 |
| 4,524,032 | A | 6/1985 | Misake et al. .............. 260/465 |
| 4,868,318 | A | 9/1989 | Scherer et al. .............. 549/362 |
| 4,996,369 | A | 2/1991 | Kalota et al. .............. 568/615 |
| 5,093,432 | A | 3/1992 | Bierschenk et al. ..... 525/331.6 |
| 5,322,903 | A | 6/1994 | Bierschenk et al. ..... 525/331.6 |
| 5,466,877 | A | 11/1995 | Moore .................. 562/852 |
| 5,488,142 | A | 1/1996 | Fall et al. .................. 560/227 |
| 5,571,870 | A | 11/1996 | Bierschenk et al. ..... 525/331.6 |
| 5,578,278 | A | 11/1996 | Fall et al. .................. 422/234 |
| 5,674,949 | A | 10/1997 | Bierschenk et al. ..... 525/331.6 |
| 5,753,776 | A | 5/1998 | Bierschenk et al. ..... 525/331.6 |
| 6,093,860 | A | 7/2000 | Watanabe et al. .......... 570/175 |
| 6,255,536 | B1 | 7/2001 | Worm et al. ............. 568/615 |
| 6,586,626 | B2 | 7/2003 | Okazoe et al. ............. 562/863 |
| 6,747,174 | B2 | 6/2004 | Okazoe et al. ............. 562/852 |
| 2002/0107358 | A1 | 8/2002 | Okazoe et al. | |
| 2003/0139570 | A1 | 7/2003 | Okazoe et al. | |
| 2003/0149309 | A1 | 8/2003 | Okazoe et al. | |
| 2003/0166969 | A1 | 9/2003 | Okazoe et al. | |
| 2003/0171616 | A1 | 9/2003 | Watanabe et al. | |
| 2003/0203501 | A1 | 10/2003 | Kawahara et al. | |
| 2003/0204099 | A1 | 10/2003 | Okazoe et al. | |
| 2003/0212297 | A1 | 11/2003 | Ito et al. | |
| 2003/0216595 | A1 | 11/2003 | Okazoe et al. | |
| 2004/0204618 | A1 | 10/2004 | Okazoe et al. | |

FOREIGN PATENT DOCUMENTS

| EP | 0 265 052 | 4/1988 |
| EP | 0 557 167 | 8/1993 |
| JP | 59-48436 | 3/1984 |
| JP | 1-216948 | 8/1989 |
| JP | 8-72069 | 3/1996 |
| JP | 10-116627 | 5/1998 |
| WO | WO 95/25082 | 9/1995 |
| WO | WO 00/56694 | 9/2000 |
| WO | WO 01/16085 | 3/2001 |
| WO | WO 01/46093 | 6/2001 |
| WO | WO 01/46107 | 6/2001 |
| WO | WO 01/94285 | 12/2001 |
| WO | WO 02/04397 | 1/2002 |
| WO | WO 02/10106 | 2/2002 |
| WO | WO 02/10107 | 2/2002 |
| WO | WO 02/10108 | 2/2002 |
| WO | WO 02/18314 | 3/2002 |
| WO | WO 02/20445 | 3/2002 |
| WO | WO 02/26679 | 4/2002 |
| WO | WO 02/26682 | 4/2002 |
| WO | WO 02/26686 | 4/2002 |
| WO | WO 02/26687 | 4/2002 |
| WO | WO 02/26688 | 4/2002 |
| WO | WO 02/26689 | 4/2002 |
| WO | WO 02/26693 | 4/2002 |
| WO | WO 02/40437 | 5/2002 |
| WO | WO 02/44138 | 6/2002 |
| WO | WO 02/055471 | 7/2002 |

OTHER PUBLICATIONS

K. Murata et al, J. Am. Chem. Soc., vol. 120, No. 28, pp. 7117–7118, 1998.
I. Tari, et al, J. Org. Chem. vol. 45, No. 7, pp. 1214–1217, 1980.
Barker et al, Biochemical Pharmacology, vol. 34, No. 10, pp. 1849–1852, 1985.
Yamabe et al, Journal of Fluorine Chemistry, 94, (1999), pp. 65–68.
U.S. Appl. No. 10/833,048, filed Apr. 28, 2004 Okazoe, et al.
U.S. Appl. No. 10/421,924, filed Apr. 24, 2003 Okazoe, et al.
U.S. Appl. No. 10/084,506, filed Feb. 28, 2002 Okazoe, et al.
U.S. Appl. No. 10/307,388, filed Dec. 2, 2002 Okazoe, et al.
U.S. Appl. No. 10/372,765, filed Feb. 26, 2003 Okazoe, et al.
U.S. Appl. No. 10/397,230, filed Mar. 27, 2003 Okazoe, et al.

(Continued)

Primary Examiner—Samuel Barts
Assistant Examiner—Sikarl A. Witherspoon
(74) Attorney, Agent, or Firm—Oblon, Spivak, McClelland, Maier & Neustadt, P.C.

(57) ABSTRACT

The present invention provides a method for obtaining a compound useful as a raw material for various fluororesins in high yield by a short process by using a starting material which is inexpensive and readily available.

23 Claims, No Drawings

OTHER PUBLICATIONS

U.S. Appl. No. 10/397,423, filed Mar. 27, 2003 Watanabe, et al.

U.S. Appl. No. 10/397,521, filed Mar. 27, 2003 Okazoe, et al.

U.S. Appl. No. 10/438,943, filed May 16, 2003 Kawahara, et al.

U.S. Appl. No. 10/442,227, filed May 21, 2003 Ito, et al.

U.S. Appl. No. 10/915,423, filed Aug. 11, 2004 Okazoe, et al.

METHOD FOR PRODUCING A FLUORINE-CONTAINING COMPOUND

This application is a Divisional of U.S. patent application Ser. No. 10/340,634, filed Jan. 13, 2003, now U.S. Pat. No. 6,894,187; which is a continuation of claims the benefit of priority under 35 U.S.C. § 365(c) to International Application No. PCT/JP01/06024, filed on Jul. 11, 2001.

TECHNICAL FIELD

The present invention relates to a method for producing an industrially useful fluorine-containing compound, particularly to a process for producing a diacyl fluoride having —COF groups at both terminals, and a compound having fluorinated vinyl groups at both terminals. Further, the present invention provides a novel intermediate useful for producing a diacyl fluoride which is useful as a precursor for a raw material of fluororesins.

BACKGROUND ART

A fluorine-containing monomer such as a perfluoro(alkyl vinyl ether) is useful as a raw material monomer for heat resistant and chemical resistant fluororesins. For example, a perfluoro(alkyl vinyl ether) having carboxyl groups in its molecule, is useful as a raw material monomer for ion exchange membranes and can be produced via a diacyl fluoride (J. Fluorine Chem., 94, 65–68 (1999)).

Further, as a method for fluorinating all of C—H portions in a hydrocarbon compound to C—F, a method wherein fluorination is carried out by means of fluorine (elemental fluorine), or a method wherein fluorination is carried out by using, as a fluorine atom source, a product formed by electrolysis of hydrogen fluoride in an electrolyzer (i.e. a method so-called an electrochemical fluorination reaction), is known. Further, a gas phase method and a liquid phase method are known for the reaction employing fluorine.

Further, a method is also known wherein a perfluorinated ester compound having at least 16 carbon atoms, is pyrolyzed to obtain an acid fluoride compound. It is disclosed that an acid fluoride compound can be produced by a method wherein a hydrocarbon type ester compound having a corresponding carbon skeleton, is fluorinated by a liquid phase method employing fluorine gas (J. Am. Chem. Soc., 120, 7117 (1998)).

Further, as a common method for producing a diacyl fluoride, the following method employing iodine and fuming sulfuric acid, is known.

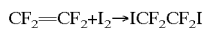

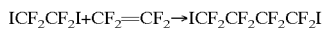

Further, a method is also disclosed wherein a diol diacetate containing no fluorine is used as the starting material, this material is directly fluorinated in 1,1,2-trichloro-1,2,2-trifluoroethane (hereinafter referred to as R-113) to produce a perfluorodiol diacetate, and then this is subjected to a dissociation reaction of the ester bond in pyridine to obtain a perfluorodiacyl compound and $CF_3COF$ (U.S. Pat. No. 5,466,877).

Further, a method is also proposed wherein $CF_2$=CF— of a compound having $CF_2$=CF— at one terminal and —COF at the other terminal, is halogenated with e.g. chlorine gas, and then, the other terminal is pyrolyzed to $CF_2$=CF—, and further by dehalogenation, $CF_2$=CF— is regenerated, to produce a compound having fluorinated vinyl groups at both terminals (JP-A-1-143843).

Further, a method for producing $CF_2$=CFOCF$_2$-CF$_2$CF=CF$_2$ by pyrolysis of a potassium salt of a dicarboxylic acid such as $KOCO(CF_2)_4OCF(CF_3)CO_2K$, is reported (J. Org. Chem., 34, 1841 (1969)).

The electrochemical fluorination reaction has had a drawback such that an isomerization reaction, cleavage and re-bonding reactions of C—C bonds, etc. are likely to take place, whereby the intended compound can not be obtained in high purity. Further, there has been a problem that when reacted with fluorine in a gas phase, C—C single bonds undergo cleavage, whereby various types of by-products tend to be formed.

It is reported that the method of carrying out the reaction with fluorine in a liquid phase, is a method for solving the problems of the gas phase method (U.S. Pat. No. 5,093,432). As a solvent for the reaction to be used for this liquid phase method, a solvent capable of dissolving fluorine, is usually employed. However, a non-fluorinated type hydrocarbon compound or a hydrocarbon compound having a small fluorine content is hardly soluble in a solvent, whereby a problem has been observed such that the reaction will not proceed smoothly. Further, in a conventional liquid phase method, the reaction is carried out at a very low concentration, whereby there has been a problem that the production efficiency is poor, the reaction will be in a suspension system which is disadvantageous to the reaction. Further, there has been a problem that when the liquid phase method is applied to a low molecular weight hydrocarbon compound, the yield by the reaction tends to be very low.

Further, the conventional method for producing a diacyl fluoride has had a problem that the price of the raw material is high, and the method is economically disadvantageous. Further, iodine, fuming sulfuric acid, etc. are used, whereby there has been a problem that the apparatus is likely to be corroded, or handling of the reagent for the reaction tends to be difficult.

Further, in a case where a diol diacetate having no fluorine, is fluorinated in a liquid phase, there has been a problem that a decomposition reaction of the raw material substrate is observed. Further, the method of employing R-113 has a problem that such a method may not be used in future.

Further, the conventional method for producing a compound having fluorinated vinyl groups at both terminals has had a drawback such that two step reactions are required to form two fluorinated vinyl groups, and the substrate for the pyrolysis is hardly available and expensive.

DISCLOSURE OF THE INVENTION

It is an object of the present invention to solve the problems of the conventional methods and to provide a method whereby a fluorine-containing compound can be produced from an inexpensive readily-available raw material compound in a short process.

Namely, the present invention provides a method for producing a fluorine-containing compound, which comprises reacting the following compound (1) with the following compound (2) to produce the following compound (3) (provided that the compound (3) is a compound having a fluorine content of at least 30 mass % and has a hydrogen atom or an unsaturated bond which can be fluorinated), fluorinating the compound (3) in a liquid phase to produce the following compound (4), followed by a cleavage reaction of $E^F$ of the compound (4) to obtain a compound (5) and/or a compound (6):

$$E^1\text{-}R^A\text{-}E^1 \tag{1}$$

$$E^2\text{-}R^B \tag{2}$$

$$R^B\text{-}E\text{-}R^A\text{-}E\text{-}R^B \tag{3}$$

$$R^{BF}\text{-}E^F\text{-}R^{AF}\text{-}E^F\text{-}R^{BF} \tag{4}$$

$$E^{F1}\text{-}R^{AF}\text{-}E^{F1} \tag{5}$$

$$R^{BF}\text{-}E^{F2} \tag{6}$$

wherein $R^A$, $R^B$: $R^A$ is a fluorine-containing bivalent organic group which is the same as $R^{AF}$, or a bivalent organic group which will be converted to $R^{AF}$ by a fluorination reaction, and $R^B$ is a monovalent organic group which is the same as $R^{BF}$, or a monovalent organic group which will be converted to $R^{BF}$ by a fluorination reaction, $R^{AF}$, $R^{BF}$: $R^{AF}$ is a fluorine-containing bivalent organic group which is the same as or different from $R^A$ and when different, it is a group having $R^A$ fluorinated, and $R^{BF}$ is a fluorine-containing monovalent organic group which is the same as or different from $R^B$, and when different, it is a group having $R^B$ fluorinated, $E^1$, $E^2$: reactive groups which will react to each other to form a bivalent connecting group (E), E: a bivalent connecting group formed by the reaction of $E^1$ and $E^2$, $E^F$: a group which is the same as E, or a group having E fluorinated, provided that at least one selected from $R^{AF}$, $R^{BF}$ and $E^F$, is a group formed by a fluorination reaction, and $E^{F1}$, $E^{F2}$: each independently is a group formed by cleavage of $E^F$.

Further, the present invention provides the method wherein the compound (5) is the following compound (5-2), and such a compound is pyrolyzed to produce the following compound (7-2):

$$FCO\text{-}Q^{F1}\text{-}R^{AF}\text{-}Q^{F2}\text{-}COF \tag{5-2}$$

$$CF_2{=}CF\text{—}R^{AF}\text{—}CF{=}CF_2 \tag{7-2}$$

wherein $R^{AF}$: as defined above, and $Q^{F1}$, $Q^{F2}$: each represents —CF(CF$_3$)— or —CF$_2$—CF$_2$—.

Further, the present invention provides a compound selected from the compounds of the following formulae:

$$CF_3CF_2COO(CH_2)_4OCOCF_2CF_3 \tag{3-12},$$

$$CF_3CF_2COOCH_2CH(CH_3)O(CH_2)_4OCOCF_2CF_3 \tag{3-13},$$

$$CF_3CF_2COO(CH_2)_2O(CH_2)_2OCOCF_2CF_3 \tag{3-14},$$

$$CF_3CF_2CF_2OCF(CF_3)COOCH_2CH(CH_3)O(CH_2)_5OCOCF(CF_3)—OCF_2CF_2CF_3 \tag{3-15},$$

$$CF_3CF_2COO(CH_2)_2O(CH_2)_2OCH(CH_3)CH_2OCOCF_2CF_3 \tag{3-16},$$

$$CF_3CF_2COOCF_2CF_2CF_2CF_2OCOCF_2CF_3 \tag{4-12},$$

$$CF_3CF_2COOCF_2CF(CF_3)OCF_2CF_2CF_2CF_2OCOCF_2CF_3 \tag{4-13},$$

$$CF_3CF_2COOCF_2CF_2OCF_2CF_2OCOCF_2CF_3 \tag{4-14},$$

$$CF_3CF_2CF_2OCF(CF_3)COOCF_2CF(CF_3)OCF_2(CF_2)_3—CF_2OCOCF(CF_3)OCF_2CF_2CF_3 \tag{4-15},$$

$$CF_3CF_2COO(CF_2)_2O(CF_2)_2OCF(CF_3)CF_2OCOCF_2CF_3 \tag{4-16},$$

$$FCOCF_2O(CF_2)_2OCF(CF_3)COF \tag{5-16}.$$

BEST MODE FOR CARRYING OUT THE INVENTION

In this specification, an organic group is a group wherein carbon atoms are essential, and it may be a saturated group or an unsaturated group. As the organic group which will be fluorinated, an atom which can be substituted by a fluorine atom (such as a hydrogen atom bonded to a carbon atom) or an atomic group which can be substituted by fluorine atoms (for example, —CF=CF— being a carbon-carbon unsaturated double bond, will be converted to CF$_2$CF$_2$— by a fluorination reaction, and —C≡C— being a carbon-carbon unsaturated triple bond will be converted to CF$_2$CF$_2$— or —CF=CF— by a fluorination reaction) may, for example, be mentioned. The organic group in the present invention is preferably one having a carbon number of from 1 to 20, particularly preferably one having a carbon number of from 1 to 10, from the viewpoint of the solubility in the liquid phase which is used for the fluorination reaction.

As the monovalent organic group, a monovalent hydrocarbon group, a hetero atom-containing monovalent hydrocarbon group, a halogenated monovalent hydrocarbon group, or a halogenated (hetero atom-containing monovalent hydrocarbon) group, is preferred. As the bivalent organic group, a bivalent hydrocarbon group, a hetero atom-containing bivalent hydrocarbon group, a halogenated bivalent hydrocarbon group, or a halogenated (hetero atom-containing bivalent hydrocarbon) group, is preferred.

The hydrocarbon group is a group comprising carbon atoms and hydrogen atoms, and the hydrocarbon group is preferably one having a carbon number of from 1 to 20, particularly preferably from 1 to 10, from the viewpoint of e.g. the solubility in a liquid phase at the time of the fluorination reaction. In the hydrocarbon group, a single bond or an unsaturated bond may be present as a carbon-carbon bond. The hydrocarbon group may be an aliphatic hydrocarbon group or an aromatic hydrocarbon group. An aliphatic hydrocarbon group is preferred. The structure of the aliphatic hydrocarbon group may be a linear structure, a branched structure, a cyclic structure or a structure having a ring structure partially. As the organic group, a saturated group wherein carbon-carbon bonds are made only of single bonds, is preferred.

In a case where the hydrocarbon group is a monovalent saturated hydrocarbon group, it may, for example, be an alkyl group, a cycloalkyl group or a monovalent saturated hydrocarbon group having a cyclic portion (such as a cycloalkyl group, a cycloalkylalkyl group or a bicycloalkyl group, a group having an alicyclic spiro structure, or a group having such a group as a partial structure), and an alkyl group is preferred. In a case where an aliphatic hydrocarbon group is an unsaturated group, a monovalent aromatic hydrocarbon group is preferred, and a phenyl group, an aryl group or such a group having a substituent, is particularly preferred.

In a case where the aliphatic hydrocarbon group is a bivalent saturated hydrocarbon group, it may be a group having one of hydrogen atoms of the above-mentioned monovalent saturated hydrocarbon group converted to a connecting bond, and it may, for example, be an alkylene group, a cycloalkylene group or a bivalent saturated hydrocarbon group having a cyclic portion (such as a bivalent saturated hydrocarbon group having, as a partial structure, a group selected from a cycloalkyl group, a bicycloalkyl group and a monovalent group having an alicyclic spiro structure, a cycloalkylene group, a bicycloalkylene group, or a bivalent saturated hydrocarbon group having, as a partial structure, a cycloalkylene group or a bicycloalkylene group), and an alkylene group is preferred. As the bivalent aromatic hydrocarbon group, a phenylene group, an arylene group or such a group having a substituent, is preferred.

In this specification, the halogen atom is a fluorine atom, a chlorine atom, a bromine atom or an iodine atom, and preferred is a fluorine atom, a chlorine atom or a bromine atom. Further, the halogenated group is a group having at least one of hydrogen atoms present in a group halogenated by at least one type of halogen atom selected from a fluorine atom, a chlorine atom, a bromine atom and an iodine atom, and it may be a group wherein hydrogen atoms are present or not present. A partially halogenated group is a group having a part of hydrogen atoms present in the group halogenated, and it is a group wherein hydrogen atoms not substituted by halogen atoms, are present. A perhalogenated group is a group having substantially all hydrogen atoms present in the group halogenated, and it is a group wherein substantially no hydrogen atom is present. Further, a perfluoro(partially fluorinated monovalent hydrocarbon) group is a group which is the same as a perfluoromonovalent saturated hydrocarbon group. Such meanings in the halogenated, the partially halogenated and the perhalogenated, are similar to the meanings in the fluorinated, the partially fluorinated, the partially chlorinated and the perfluorinated.

In this specification, the halogenated hydrocarbon group is a group having at least one of hydrogen atoms in a hydrocarbon group substituted by a halogen atom, and it is preferably a halogenated alkyl group. The halogen atom in the halogenated alkyl group is preferably a fluorine atom, a chlorine atom or a bromine atom. Further, as a partially halogenated monovalent saturated hydrocarbon group, a partially halogenated alkyl group is preferred. As a perhalogenated monovalent hydrocarbon group, a perhalogenated alkyl group is preferred. The halogen atoms in a perhalogenated alkyl group are preferably composed solely of fluorine atoms, or fluorine atoms and halogen atoms other than fluorine atoms (preferably chlorine atoms).

A halogenated bivalent saturated hydrocarbon group is a group having at least one of hydrogen atoms in a bivalent saturated hydrocarbon group substituted by a halogen atom, and it is preferably a halogenated alkylene group. As the halogen atom in the halogenated alkylene group, a fluorine atom, a chlorine atom or a bromine atom is preferred. As a partially halogenated bivalent saturated hydrocarbon group, a partially halogenated alkylene group is preferred. As a perhalogenated bivalent saturated hydrocarbon group, a perhalogenated alkylene group is preferred. The halogen atoms in the perhalogenated alkylene group may all be fluorine atoms or may comprise fluorine atoms and halogen atoms other than fluorine atoms (preferably chlorine atoms).

In this specification, the hetero atom-containing saturated hydrocarbon group is a saturated hydrocarbon group which contains a hetero atom not changed by a fluorination reaction or a hetero atom group not changed by a fluorination reaction. As a bivalent hetero atom not changed by a fluorination reaction, an etheric oxygen atom is preferred, and as a bivalent hetero atom group not changed by a fluorination reaction, —C—C(O)—C— or —C—SO$_2$—C— may, for example, be mentioned.

As a hetero atom-containing monovalent saturated hydrocarbon group, an alkyl group having an etheric oxygen atom inserted between a carbon-carbon bond, or a cycloalkyl group having an etheric oxygen atom inserted between a carbon-carbon bond, may, for example, be mentioned (provided that the etheric oxygen atom in the group may be one or more), and particularly preferred is an alkoxyalkyl group.

As a hetero atom-containing bivalent saturated hydrocarbon group, an alkylene group having an etheric oxygen atom inserted between a carbon-carbon bond or at the bonding terminal of the group, or a cycloalkylene group having an etheric oxygen atom inserted between a carbon-carbon bond, may, for example, be mentioned, and particularly preferred is an oxyalkylene group or a polyoxyalkylene group.

As a halogenated (hetero atom-containing monovalent saturated hydrocarbon) group, a group having at least one of hydrogen atoms in the above-mentioned hetero atom-containing monovalent saturated hydrocarbon group substituted by a halogen atom, may be mentioned, and a halogenated (alkoxyalkyl) group is preferred.

As a halogenated (hetero atom-containing bivalent saturated hydrocarbon) group, a group having at least one of hydrogen atoms in the above-mentioned hetero atom-containing bivalent saturated hydrocarbon group substituted by a halogen atom, may be mentioned, and a halogenated (oxyalkylene) group or a halogenated (polyoxyalkylene) group is preferred.

As specific examples of these groups, groups in the following specific compounds may be mentioned.

$R^A$ in the compound (1) is a fluorine-containing bivalent organic group which is the same as $R^{AF}$, or a bivalent organic group which will be converted to $R^{AF}$ by a fluorination reaction. The carbon number of $R^A$ is preferably from 1 to 20, particularly preferably from 1 to 10. $R^A$ may have a linear structure, a branched structure, a cyclic structure or a structure partially having a ring.

$R^A$ is preferably a bivalent saturated hydrocarbon group, a halogenated bivalent saturated hydrocarbon group, a hetero atom-containing bivalent saturated hydrocarbon group or a halogenated (hetero atom-containing bivalent saturated hydrocarbon) group, or preferably such a group containing hydrogen atoms. Further, $R^A$ is preferably a group which is different from the following $R^{AF}$, i.e. a group which will be converted to $R^{AF}$ by a fluorination reaction.

In a case where $R^A$ is a group containing hydrogen atoms, it is preferably a bivalent saturated hydrocarbon group, a partially halogenated bivalent saturated hydrocarbon group, a hetero atom-containing bivalent saturated hydrocarbon group or a partially halogenated (hetero atom-containing bivalent saturated hydrocarbon) group, and it is preferably an alkylene group, a partially fluorinated alkylene group, a partially fluorinated (partially chlorinated alkylene) group, an alkylene group containing an etheric oxygen atom (e.g. an oxyalkylene group), a partially fluorinated alkylene group having an etheric oxygen atom (e.g., a partially fluorinated oxyalkylene group), a partially fluorinated (partially chlorinated alkylene) group containing an etheric oxygen atom (e.g., a partially fluorinated (partially chlorinated oxyalkylene) group). The etheric oxygen atom is preferably inserted at one or more positions selected from between a carbon-carbon bond, at the bonding terminal with $E^1$ and at the bonding terminal with $E^2$.

Further, in a case where $R^A$ is a group other than the above, it is preferably a group having a fluorine atom in the desired $R^{AF}$ substituted by a monovalent hetero atom group (e.g. a carboxyl group or the like) which can be converted to a fluorine atom by a fluorination reaction (e.g. a group having —C(O)— inserted between a carbon-carbon bond of an alkylene group, or the like) or a group having at least one of carbon-carbon single bonds in the desired $R^{AF}$ substituted by a carbon-carbon double bond or a carbon-carbon triple bond.

It is preferred that hydrogen atoms or fluorine atoms are bonded to the carbon atoms forming the carbon-carbon double bond, and it is particularly preferred that hydrogen atoms are bonded. To the carbon atoms forming an unsaturated bond, fluorine atoms will be added by a fluorination reaction in a liquid phase, and hydrogen atoms will be substituted by fluorine atoms. For example, a phenylene group may be changed to a perfluorocyclohexylene group by a fluorination reaction. As a specific example of such a group, a cyclohexenylene group, a phenylene group, an alkenylene group or an alkynylene group, may, for example, be mentioned.

$E^1$ in the compound (1) is a reactive group which will react with $E^2$ to form a bivalent connecting group (E). Such a bivalent connecting group (E) may be a group which may be changed or may not be changed by a fluorination reaction.

As the bivalent connecting group (E), —CH$_2$OCO— or —CH$_2$OSO$_2$— (provided that the direction of such a group is not limited) is, for example, preferred, and —CH$_2$OCO— is particularly preferred from the viewpoint of the usefulness of the desired compound. In a case where E is the preferred group, $E^1$ and $E^2$ may be such that one of them is —CH$_2$OH, and the other is —COX (X is a halogen atom) or —SO$_2$X.

Now, a detailed description will be made with reference to a case where the bivalent connecting group (E) is —CH$_2$OCO—.

In the present invention, the compound (5) which used to be difficult to obtain, can be produced by carrying out the reaction of the present invention by using the compound (1) having a group ($R^A$) having a carbon skeleton corresponding to $R^{AF}$ of the desired compound (5). The structure of the compound (1) which can be used in the present invention, is not particularly limited.

An example of the compound (5) which used to be difficult to obtain, may be a compound (5) wherein the structure of $R^{AF}$ is complex, or a low molecular weight fluorinated product (5) whereby many by-products are formed by a fluorination reaction. As the low molecular weight compound (5), a fluorinated product of the compound (1) having a molecular weight of at most 200 (preferably a molecular weight of from 50 to 200), may be mentioned. Namely, the method of the present invention which is carried out by using the compound (1) having a molecular weight of at most 200, is one of preferred embodiments.

As the compound (1), the following compound (1-1) wherein $E^1$ is —CH$_2$OH, is preferred, the following compound (1-10) wherein $R^A$ is $R^{AH1}$ is more preferred, and the following compound (1-11) wherein $R^A$ is $R^{AH2}$, is particularly preferred.

HO—CH$_2$—$R^A$—CH$_2$OH (1-1),

HO—CH$_2$—$R^{AH1}$—CH$_2$OH (1-10),

HO—CH$_2$—$R^{AH2}$—CH$_2$OH (1-11).

wherein $R^A$ has the same meaning as the meaning in the compound (1), and $R^{AH1}$ is a bivalent saturated hydrocarbon group, a halogenated bivalent saturated hydrocarbon group, a hetero atom-containing bivalent saturated hydrocarbon group or a halogenated (hetero atom-containing bivalent saturated hydrocarbon) group. $R^{AH1}$ is preferably an alkylene group, an oxyalkylene group, a polyoxyalkylene group, a halogenated alkylene group, a halogenated (oxyalkylene) group or a halogenated (polyoxyalkylene) group. In a case where such a group has a halogen atom, it is preferably at least one member selected from halogen atoms other than a fluorine atom, and as such a halogen atom, a chlorine atom, a bromine atom, or a chlorine atom and a bromine atom, are preferred.

$R^{AH2}$ is an alkylene group, or a group having an etheric oxygen atom inserted at one or more positions between a carbon-carbon bond in an alkylene group. Particularly preferably, $R^{AH2}$ is an alkylene group, an oxyalkylene group or a polyoxyalkylene group.

In the present invention, it is preferred that one of the compounds (1) and compounds (2) is a compound containing a fluorine atom, and the other is a compound containing no fluorine atom. Particularly from the viewpoint of the usefulness of the compounds, it is preferred that the compound (1) is a compound containing no fluorine atom (i.e. a compound having a fluorine content of 0 mass %), and the compound (2) is a compound containing a fluorine atom.

The following compounds may be mentioned as specific examples of the compound (1). The following compounds are known compounds or compounds which can easily be prepared by known methods from known compounds. Here, n is an integer of at least 3, preferably from 4 to 10, m is an integer of at least 1, preferably from 1 to 10, p is an integer of at least 3, preferably an integer of from 3 to 5, k is an integer of at least 1, preferably from 1 to 10, and r is an integer of at least 3, preferably an integer of from 3 to 5.

HO(CH$_2$)$_n$OH,

HO[CH$_2$CH(CH$_3$)O]$_m$(CH$_2$)$_p$OH,

HO(CH$_2$CH$_2$O)$_k$(CH$_2$)$_r$OH.

In the present invention, the compound (1) and the compound (2) are reacted. $R^B$ in the compound (2) is a monovalent organic group which is the same as $R^{BF}$, or a monovalent organic group which will be converted to $R^{BF}$ by a fluorination reaction. It is preferred to adjust the structure of $R^B$ in relation with the structure of $R^A$, so that the fluorine content in the resulting compound (3) would be at least 30 mass %.

The carbon number of $R^B$ is preferably from 2 to 20, particularly preferably from 2 to 10. If the carbon number of $R^B$ is 1, there will be a problem that the recovery of the compound (6), particularly the compound (6-1), tends to be difficult. Accordingly, the carbon number of $R^B$ is preferably at least 2. $R^B$ may have a linear structure, a branched structure, a cyclic structure, or a structure partially having a ring.

$R^B$ may be a monovalent saturated hydrocarbon group, a halogenated monovalent saturated hydrocarbon group, a hetero atom-containing monovalent saturated hydrocarbon group or a halogenated (hetero atom-containing monovalent saturated hydrocarbon) group, and it may be an alkyl group, a fluoroalkyl group, a fluoro(partially chlorinated alkyl) group, a group having an etheric oxygen atom inserted at one or more positions between carbon-carbon atoms in an alkyl group, a group having an etheric oxygen atom inserted at one or more positions between carbon-carbon atoms in a fluoroalkyl group, or a group having an etheric oxygen atom inserted at one or more positions between carbon-carbon atoms in a fluoro(partially chlorinated alkyl) group.

In a case where $R^B$ is a group other than the above, it may be a group having a fluorine atom in the desired $R^{BF}$ substituted by a monovalent hetero atom group which can be converted to a fluorine atom by a fluorination reaction, or a group having at least one carbon-carbon single bond in the desired $R^{BF}$ substituted by a carbon-carbon double bond or a carbon-carbon triple bond. It is preferred that hydrogen atoms or fluorine atoms are bonded to the carbon atoms forming the carbon-carbon double bond, and it is particularly preferred that hydrogen atoms are bonded thereto. As a specific example of such $R^B$, a cyclohexenyl group, a phenyl group, an alkenyl group or an alkynyl group, may be mentioned. Further, as the monovalent hetero atom group, a carboxyl group may be mentioned, and as the group having a monovalent hetero atom group, a group having —C(O)— inserted between a carbon-carbon bond in an alkyl group (—C—C(O)—C—) may be mentioned.

With respect to $R^B$ in the present invention, in order to facilitate the after-mentioned continuous process, $R^A$ is preferably a group containing no fluorine atom, and $R^B$ is preferably a group containing a fluorine atom. Further, it is particularly preferred for carrying out the after-mentioned continuous reaction that $R^B$ is the same group as $R^{BF}$, and it is particularly preferred that $R^B$ is a perfluoromonovalent organic group. In the case of the perfluoromonovalent organic group, it is preferably a perfluoromonovalent saturated hydrocarbon group, a perfluoro(partially halogenated monovalent saturated hydrocarbon) group, a perfluoro(hetero atom-containing monovalent saturated hydrocarbon) group, or a perfluoro(partially halogenated(hetero atom-containing monovalent saturated hydrocarbon)) group. Particularly preferred is such a group having at least two carbon atoms.

As the compound (2), a commercial product may be employed, or a compound (6) formed by the after-mentioned method of the present invention, may be employed.

Further, in the present invention, the fluorine content in the compound (3) (the fluorine content is a proportion of fluorine atoms to the molecular weight of the compound) is adjusted to be at least 30 mass %. By adjusting the fluorine content to be at least 30 mass %, the fluorination reaction in a liquid phase can easily be carried out in a homogeneous system, and there is a merit that the yield of the reaction will also be improved.

$E^2$ in the compound (2) is a reactive group which will react to $E^1$ to form a bivalent connecting group (E), and it is particularly preferably —COX or —SO$_2$X (X is a halogen atom, preferably a chlorine atom or a fluorine atom, and in a case where the after-mentioned continuous process is carried out, X is a fluorine atom). Further, the compound (2) is preferably a compound (2-1) wherein $E^2$ is —COX, more preferably a compound (2-10) wherein $R^B$ is the following $R^{BF1}$, particularly preferably a compound (2-11) wherein $R^B$ is $R^2$.

$$XCOR^B \qquad (2\text{-}1),$$

$$FCOR^{BF1} \qquad (2\text{-}10),$$

$$FCOR^2 \qquad (2\text{-}11).$$

Here, $R^B$ has the same meaning as the meaning in the compound (2), $R^{BF1}$ is a perfluoromonovalent saturated hydrocarbon group or a perfluoro(hetero atom-containing monovalent saturated hydrocarbon) group, and $R^2$ is a perfluoroalkyl group, a perfluoro(partially chlorinated alkyl) group, a perfluoro(alkoxyalkyl) group or a perfluoro(partially chlorinated alkoxyalkyl) group. The carbon number of $R^{BF1}$ and $R^2$ is preferably from 2 to 20, particularly preferably from 2 to 10.

The perfluoromonovalent saturated hydrocarbon group may, for example, be —CF$_2$CF$_3$, —CF$_2$CF$_2$CF$_3$, —CF$_2$CF$_2$CF$_2$CF$_3$, —CF$_2$CClF$_2$, —CF$_2$CBrF$_2$, —CF$_2$CFClCF$_2$Cl, —CF(CF$_3$)$_2$, —CF$_2$CF(CF$_3$)$_2$, —CF(CF$_3$)CF$_2$CF$_3$ or —C(CF$_3$)$_3$.

The perfluoro(hetero atom-containing monovalent saturated) group may, for example, be —CF(CF$_3$)OCF$_2$CF$_2$CF$_3$, —CF(CF$_3$)OCF$_2$CF$_2$CFClCF$_2$Cl or —CF(CF$_3$)OCF$_2$CF$_2$Br.

The following compounds may be mentioned as specific examples of the compound (2).

CF$_3$CF$_2$COF,

CF$_2$ClCFClCF$_2$COF,

CF$_2$ClCF$_2$CFClCOF,

CF$_3$CF$_2$CF$_2$OCF(CF$_3$)COF,

CF$_2$ClCFClCF$_2$CF$_2$OCF(CF$_3$)COF,

CClF$_2$CF$_2$COF,

CBrF$_2$CF$_2$COF,

CF$_2$BrCF$_2$OCF(CF$_3$)COF,

CF$_2$ClCFClCF$_2$CF(CF$_3$)OCF(CF$_3$)COF,

CF$_3$CF$_2$CF$_2$OCF(CF$_3$)CF$_2$OCF(CF$_3$)COF,

CH$_3$CH$_2$CH$_2$OCF(CF$_3$)COF,

CH$_2$ClCHClCH$_2$COCl,

CF$_3$CF$_2$CF$_2$OCF$_2$CF$_2$COF.

The compound (2) may be a known compound or can be produced by a known method from a known compound. For example, CF$_3$CF$_2$CF$_2$OCF(CF$_3$)COF is readily available as an intermediate for a perfluoro(alkyl vinyl ether).

The reaction of the compound (1) with the compound (2) may be carried out by applying a known reaction method and conditions depending upon the structures of $E^1$ and $E^2$ and their combination. For example, the reaction of the compound (1-1) wherein $E^1$ is —CH$_2$OH, with the compound (2-1) wherein $E^2$ is —COX, can be carried out under the conditions for a known esterification reaction. The esterification reaction may be carried out in the presence of a solvent (hereinafter referred to as an esterification reaction solvent), but is preferably carried out in the absence of any esterification reaction solvent, from the viewpoint of the volume efficiency.

In a case where an esterification reaction solvent is employed, it is preferably dichloromethane, chloroform, triethylamine or a mixed solvent of triethylamine and tetrahydrofuran. The amount of the esterification reaction solvent to be used, is preferably from 50 to 500 mass %, based on the total amount of the compound (1-1) and the compound (2-1).

By the reaction of the compound (1-1) with the compound (2-1), an acid represented by HX, will be formed. In a case where as the compound (2-1), a compound wherein X is a fluorine atom, is used, HF will be formed, and accordingly, an alkali metal fluoride (NaF or KF is preferred) or a trialkylamine may, for example, be present in the reaction system as a HF scavenger. It is advisable to use a HF scavenger in a case where the compound (1-1) or the compound (2-1) is a compound which is unstable to an acid. Further, in a case where a HF scavenger is not used, it is preferred to carry out the reaction at a reaction temperature at which HF can be vaporized, and HF is discharged out of the reaction system as carried by a nitrogen stream. The HF scavenger is used preferably in an amount of from 1 to 10 times by mol to the compound (2-1).

In the esterification reaction, the amount of the compound (2-1) to the compound (1-1) is preferably from 1.5 to 10 times by mol, particularly preferably from 2 to 5 times by mol. The lower limit of the temperature for the reaction of the compound (1-1) with the compound (2-1) is preferably −50° C., and the upper limit is preferably whichever is lower between +100° C. and the boiling point of the solvent. Further, the reaction time may suitably be changed depending upon the supply rates of the raw materials and the amounts of the compounds to be used in the reaction. The reaction pressure is preferably from 0 to 2 MPa (gauge pressure).

By the reaction of the compound (1) with the compound (2), the compound (3) will be formed. In the compound (3), $R^A$ is the same group as $R^A$ in the compound (1), and $R^B$ is the same group as $R^B$ in the compound (2). E is a bivalent connecting group formed by the reaction of $E^1$ with $E^2$, and may, for example, be —$CH_2OCO$— or —$CH_2SO_2$—.

Further, since the fluorine content in the compound (3) is at least 30 mass %, at least one of $R^A$, $R^B$ and E is a group containing fluorine atoms. Further, the compound (3) preferably has a molecular weight of more than 200 and not more than 1000, so that the fluorination reaction in a liquid phase in the next step can be carried out smoothly. If the molecular weight is too small, the compound (3) tends to be readily vaporized, whereby a decomposition reaction in a gas phase is likely to take place during the fluorination reaction. On the other hand, if the molecular weight is too large, it tends to be difficult to handle or purify the compound (3).

It is preferred to suitably change the fluorine content depending upon the type of the liquid phase to be used for the fluorination reaction. Usually, the fluorine content is preferably adjusted to from 30 to 86 mass %, particularly preferably from 30 to 76 mass %. The compound (3) having a fluorine content of at least the specified amount, is a compound which is especially excellent in the solubility in the liquid phase for the fluorination reaction and which is excellent in the operation efficiency for the fluorination reaction and is capable of accomplishing the reaction at a high reaction yield.

The compound (3) is preferably a compound (3-1) which will be formed by a reaction of the compound (1-1) with the compound (2-1), more preferably a compound (3-10) which will be formed by the reaction of the compound (1-10) with the compound (2-10), particularly preferably a compound (3-11) which will be formed by the reaction of the compound (1-11) with the compound (2-11).

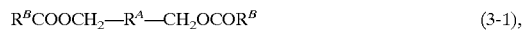  (3-1),

  (3-10),

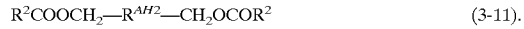  (3-11).

Here, $R^A$, $R^B$, $R^{AH1}$, $R^{BF1}$, $R^2$ and $R^{AH2}$ are as defined above, and their preferred embodiments are also the same.

The following compounds may be mentioned as specific examples of the compound (3). Here, the symbols in the formulae are as defined above.

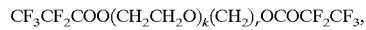

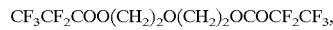

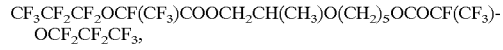

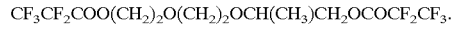

The crude product containing the compound (3) formed by the reaction of the compound (1) with the compound (2), may be purified or may be used directly for e.g. the subsequent reaction, depending upon the purpose. It is preferred to carry out purification from the viewpoint of carrying out the fluorination reaction smoothly in the subsequent step.

The purification method may, for example, be a method of directly distilling the crude product, a method of treating the crude product with a diluted alkali aqueous solution, followed by liquid separation, a method of extracting the crude product with a suitable organic solvent, followed by distillation or silica gel column chromatography.

In the present invention, the compound (3) is then fluorinated. The fluorination reaction may be carried out by electrochemical fluorination or gas phase fluorination, but fluorination in a liquid phase is preferred. Fluorination in a liquid phase is an excellent method whereby the compound (4) can be formed in high yield, while preventing the decomposition reaction of the compound (3). Now, the following description will be made with reference to a case where fluorination is carried out by a liquid phase fluorination method wherein the reaction with fluorine is carried out in a liquid phase.

The liquid phase fluorination method is a method which comprises reacting the compound (3) with fluorine in a liquid phase. The liquid phase may be formed of a substrate or a product of a reaction, and it is usually preferred that a solvent (hereinafter referred to as a fluorination reaction solvent) is essential. As the fluorine, fluorine gas, or fluorine gas diluted with an inert gas, is preferably employed. As the inert gas, nitrogen gas or helium gas is preferred, and nitrogen gas is particularly preferred from such a viewpoint that it is economically advantageous. The amount of fluorine gas in the nitrogen gas is not particularly limited, but it is preferably at least 10 vol %, from the viewpoint of efficiency, particularly preferably at least 20 vol %.

As the fluorination reaction solvent, a solvent which essentially contains a C—F bond without containing a C—H bond, is preferred. Particularly preferred is a perfluoroalkane or an organic solvent having a known organic solvent containing at least one atom selected from a chlorine atom, a nitrogen atom and an oxygen atom in its structure, perfluorinated. Further, as the fluorination reaction solvent, it is preferred to employ a solvent which provides a high solubility of the compound (3). Particularly preferred is a solvent capable of dissolving at least 1 mass % of the compound (3), and especially preferred is a solvent capable of dissolving at least 5 mass % thereof.

Examples of the fluorinated reaction solvent include the after-mentioned compound (5), the compound (6), perfluoroalkanes (tradename: FC-72, etc.), perfluoroethers (tradename: FC-75, FC-77, etc.), perfluoropolyethers (tradename: KRYTOX, FOMBLIN, GALDEN, DEMNUM, etc.), chlorofluorocarbons (tradename: FLON LUBE), chlorofluoropolyethers, perfluoroalkylamines (for example, perfluorotrialkylamine, etc.), and an inert fluid (tradename: FLUORINERT). A perfluorotrialkylamine, the compound (5) or the compound (6) is preferred. It is particularly preferred to use the compound (5) or the compound (6), whereby work-up process after the reaction will be easy.

The amount of the fluorinated reaction solvent is preferably at least 5 times by mass, particularly preferably from 10 to 100 times by mass, to the compound (3).

The reaction system for the fluorination reaction is preferably a batch system or a continuous system. Further, the fluorination reaction is preferably carried out by the method 2 which will be described hereinafter, from the viewpoint of the reaction yield and selectivity. Further, the fluorine gas is preferably used as diluted by an inert gas such as nitrogen gas, whether it is carried out by a batch system or by a continuous system.

Method 1: A method wherein the compound (3) and the fluorinated reaction solvent are charged to a reactor, stirring is initiated, and the reaction is carried out while continuously supplying fluorine gas to the fluorinated reaction solvent at a prescribed reaction temperature and reaction pressure.

Method 2: A method wherein the fluorination solvent is charged into a reactor and stirred, and then the fluorine gas, the compound (3) and the fluorination reaction solvent are continuously supplied to the fluorination reaction solvent in a prescribed molar ratio, under prescribed reaction temperature and reaction pressure.

When the compound (3) is supplied in the method 2, it is preferred to supply the compound (3) which is diluted with the fluorination reaction solvent, with a view to improving the selectivity and suppressing the amount of by-products. Further, when the compound (3) is diluted with a solvent in the method 2, it is preferred to adjust the amount of the fluorination reaction solvent to the compound (3) to a level of at least 5 times by mass, particularly preferably at least 10 times by mass.

In either a batch system or in a continuous system, in the fluorination reaction, the amount of fluorine ($F_2$) is preferably adjusted to be always in an excess amount, to the hydrogen atoms in the compound (3). Namely, the amount of fluorine is preferably at least 1.1 times by equivalent (i.e. at least 1.1 times by mol), particularly preferably at least 1.5 times by equivalent (i.e. at least 1.5 times by mol), from the viewpoint of the selectivity. The amount of fluorine is preferably in an excess amount from the beginning to the end of the reaction. Accordingly, when the fluorination solvent is charged to the reactor at the beginning of the reaction, it is preferred that a sufficient amount of fluorine is preliminarily dissolved in the fluorination solvent.

The fluorination reaction is carried out under such a condition that the bivalent connecting group (E) will not be cleaved. In a case where the bivalent connecting group (E) is —$CF_2OCO$—, the lower limit of the reaction temperature is preferably −60° C., and the upper limit is preferably the boiling point of the compound (3). Further, from the viewpoint of the reaction yield, the selectivity and industrial applicability, the reaction temperature is particularly preferably from −50° C. to +100° C., especially preferably from −20° C. to +50° C. The reaction pressure for the fluorination reaction is not particularly limited, and it is particularly preferably from atmospheric pressure to 2 MPa (gauge pressure), from the viewpoint of the reaction yield, the selectivity and industrial applicability.

Further, in order to let the fluorination reaction proceed efficiently, it is preferred to add a C—H bond-containing compound to the reaction system, or to carry out ultraviolet irradiation. Such is preferably carried out at a later stage of the fluorination reaction, whereby the compound (3) present in the reaction system can efficiently be fluorinated, and the conversion can remarkably be improved.

The C—H bond-containing compound is preferably an organic compound other than the compound (3), particularly preferably an organic hydrocarbon, especially preferably benzene, toluene or the like. The amount of the C—H bond-containing compound is preferably from 0.1 to 10 mol %, particularly preferably from 0.1 to 5 mol %, to the hydrogen atoms in the compound (3).

Further, the C—H bond-containing compound is preferably added to the reaction system wherein fluorine is present. Further, in a case where the C—H bond-containing compound is added, it is preferred to pressurize the reaction system. The pressure for pressurizing is preferably from 0.01 to 5 MPa (gauge pressure). The time for ultraviolet irradiation is preferably from 0.1 to 3 hours.

By the fluorination reaction of the compound (3), the compound (4) will be formed. $R^{AF}$ in the compound (4) is a fluorine-containing bivalent organic group which is the same as or different from $R^A$, and when different, it is a group having $R^A$ fluorinated. $R^{BF}$ is a fluorine-containing monovalent organic group which is the same as or different from $R^B$, and when different, it is a group having $R^B$ fluorinated.

For example, when $R^A$ and $R^B$ in the compound (3) are groups having hydrogen atoms, respectively, $R^{AF}$ and $R^{BF}$ wherein such hydrogen atoms are substituted by fluorine atoms by the fluorination reaction, are groups different from $R^A$ and $R^B$, respectively. On the other hand, in a case where $R^A$ and $R^B$ are groups having no hydrogen atom (for example, in the case of perhalogenated groups), $R^{AF}$ and $R^{BF}$ are the same groups as $R^A$ and $R^B$, respectively.

$R^{AF}$ and $R^{BF}$ are preferably groups formed by the fluorination reaction, and in such groups, non-substituted hydrogen atoms may be present or may not be present, and they are preferably not substantially present. The amount of hydrogen atoms in $R^{AF}$ and $R^{BF}$ is preferably changed suitably depending upon the particularly purpose.

In the fluorination reaction in a liquid phase, it is difficult to adjust the positions at which fluorine atoms are introduced. Accordingly, when the compound (3) wherein $R^A$ and $R^B$ are, respectively, groups having hydrogen atoms, is employed, it is preferred that $R^{AF}$ and $R^{BF}$ in the compound (4) are groups which are substantially perfluorinated.

$R^{AF}$ in the compound (4) is preferably a bivalent saturated hydrocarbon group, a partially halogenated bivalent saturated hydrocarbon group, a hetero atom-containing bivalent saturated hydrocarbon group, or a group having at least one hydrogen atom in $R^A$ as a partially halogenated (hetero atom-containing bivalent saturated hydrocarbon) group, substituted by a fluorine atom by the fluorination reaction, and particularly preferred is a group having all of hydrogen atoms are substituted by fluorine atoms. Particularly preferably, $R^{AF}$ is a perfluoroalkylene group, or a group having an etheric oxygen atom inserted between carbon-carbon atoms in a perfluoroalkylene group.

$R^{BF}$ is preferably a monovalent saturated hydrocarbon group, a halogenated monovalent saturated hydrocarbon group, a hetero atom-containing monovalent saturated hydrocarbon group, or a group having at least one hydrogen atom in a halogenated (hetero atom-containing monovalent saturated hydrocarbon) group substituted by a fluorine atom, and particularly preferred is a group having all of hydrogen atoms substituted by fluorine atoms, and especially preferred is the same group as in the case where $R^B$ is a perfluorinated monovalent organic group.

$E^F$ is a group which is the same as E, or a group having E fluorinated. As an example of the case where E is a fluorinated group, a group having at least one hydrogen atom present in E substituted by fluorine, may be mentioned. As $E^F$ in a case where E is a group having a —CH═CH— moiety, a group having such a moiety converted to —$CF_2CF_2$—, may, for example, be mentioned. Further, since the compound (4) is not of the same structure as the compound (3), at least one selected from $R^{AF}$, $R^{BF}$ and $E^F$, is a group formed by the fluorination reaction, or a group having $R^A$, $R^B$ or E changed.

The compound (4) is preferably a compound (4-1) which will be formed by fluorination of the compound (3-1), more preferably a compound (4-10) having the compound (3-10)

completely fluorinated, particularly preferably a compound (4-11) having the compound (3-11) completely fluorinated.

$$R^{BF}COOCF_2-R^{AF}-CF_2OCOR^{BF} \quad (4\text{-}1)$$

$$R^{BF1}COOCF_2-R^{AF1}-CF_2OCOR^{BF1} \quad (4\text{-}10)$$

$$R^2COOCF_2-R^{AF2}-CF_2OCOR^2 \quad (4\text{-}11)$$

Here, $R^{BF}$, $R^{AF}$, $R^{BF1}$ and $R^2$ are as defined above. $R^{AF1}$ is a group corresponding to $R^{AH1}$, and in a case where hydrogen atoms are present in $R^{AH1}$, it is a group having substantially all of the hydrogen atoms substituted by fluorine atoms, and in a case where no hydrogen atom is present in $R^{AH1}$, it is the same group as $R^{AH1}$. $R^{AF2}$ is a group corresponding to $R^{AH2}$ and is a group having all of hydrogen atoms in $R^{AH2}$ substituted by fluorine atoms.

The following compounds may be mentioned as specific examples of the compound (4).

$$CF_3CF_2COOCF_2CF_2CF_2CF_2OCOCF_2CF_3,$$

$$CF_3CF_2COOCF_2CF(CF_3)OCF_2CF_2CF_2CF_2OCOCF_2CF_3,$$

$$CF_3CF_3CF_2OCF(CF_3)COOCF_2CF(CF_3)OCF_2CF_2CF_2CF_2\text{-}\\OCO-CF(CF_3)OCF_2CF_2CF_3,$$

$$CF_3CF_2COOCF_2CF(CF_3)OCF_2CF_2CF_2CF_2CF_2OCOCF_2CF_3,$$

$$CF_3CF_2COOCF_2CF_2OCF_2CF_2OCOCF_2CF_3,$$

$$CF_3CF_2COO(CF_2)_2O(CF_2)_2OCF(CF_3)CF_2OCOCF_2CF_3.$$

If a hydrogen atom in the compound (3) is substituted by a fluorine atom in the reaction for fluorinating the compound (3) in a liquid phase, HF will be formed as a by-product. To remove the by-product HF, it is preferred to let a HF scavenger coexist in the reaction system or to let the discharge gas contact with a HF scavenger at the gas outlet of the reactor. As such a HF scavenger, the same ones as mentioned above may be employed, and NaF is preferred.

In a case where a HF scavenger is permitted to coexist in the reaction system, its amount is preferably from 1 to 20 times by mol, particularly preferably from 1 to 5 times by mol to the total amount of hydrogen atoms present in the compound (3). In the case where the HF scavenger is placed at the gas outlet of the reactor, it is advisable to arrange (a) a cooler (preferably to maintain the temperature at from 10° C. to room temperature, particularly preferably at about 20° C.), (b) a packed layer of NaF pellets and (c) a cooler (preferably to maintain the temperature from −78° C. to +10° C., more preferably from −30° C. to 0° C.) in series in the order of (a)–(b)–(c). Further, a liquid returning line to return the condensed liquid from the cooler (c) to the reactor, may be provided.

The crude product containing the compound (4) obtained by the fluorination reaction, may be used directly for the subsequent step, or may be purified to one having a high purity. The purification method may, for example, be a method wherein the crude product is distilled directly under atmospheric pressure or reduced pressure.

In the present invention, by the next cleavage reaction of $E^F$ of the compound (4), the compound (5) and/or the compound (6) will be obtained. $E^F$ is cleaved to form $E^{F1}$ and $E^{F2}$. The method and conditions for the cleavage reaction may be suitably changed depending upon the structure of the compound (4). In a case where the compound (4) is the compound (4-1), the cleavage reaction is a dissociation reaction of the ester bond i.e. a reaction wherein —$CF_2OCO$— is cleaved to form two —COF.

The dissociation reaction of the ester bond of the compound (4-1) is preferably carried out by a pyrolysis or by a dissociation reaction carried out in the presence of a nucleophilic agent or an electrophilic agent. By such a reaction, the compound (5-1) and the compound (6-1) wherein $E^{F1}$ and $E^{F2}$ are —COF, will be formed.

The pyrolysis can be carried out by heating the compound (4-1). It is advisable to select the reaction type for the pyrolysis depending upon the boiling point and the stability of the compound (4-1).

For example, in a case where a volatile compound (4-1) is to be pyrolyzed, a gas phase pyrolysis may be adopted wherein it is continuously pyrolyzed in a gas phase, and the outlet gas containing the compound (5-1) and the compound (6-1) is condensed and recovered.

The reaction temperature for the gas phase pyrolysis is preferably from 50 to 350° C., more preferably from 50 to 300° C., particularly preferably from 150 to 250° C. Further, an inert gas which will not be involved directly in the reaction, may be present in the reaction system. As such an inert gas, nitrogen gas or carbon dioxide gas may, for example, be mentioned. It is preferred that the inert gas is added in an amount of from about 0.01 to 50 vol %, based on the compound (4-1). If the amount of the inert gas is large, the recovered amount of the product may decrease. The method and conditions for the gas phase pyrolysis are applicable to compounds included in the scope of the compound (4-1).

On the other hand, in a case where the compound (4-1) is a hardly volatile compound, it is advisable to employ a liquid phase pyrolysis wherein it is heated in the state of a liquid in the reactor. In such a case, the reaction pressure is not particularly limited. In a usual case, the product containing the compound (5-1) is of a low boiling point, and accordingly, it is preferred to obtain it by a method by a reaction distillation system wherein the product is vaporized and continuously withdrawn. Otherwise, a method may be employed wherein after completion of the heating, the product is withdrawn all at once from the reactor. The reaction temperature for this liquid phase pyrolysis is preferably from 50 to 300° C., particularly preferably from 100 to 250° C.

In a case where the pyrolysis is carried out by the liquid phase pyrolysis, it may be carried out in the presence or absence of a solvent (hereinafter referred to as a dissociation reaction solvent). It is preferably carried out in the absence of any solvent. The dissociation reaction solvent is not particularly limited, so long as it is one which will not react with the compound (4-1) and is compatible with the compound (4-1) and which will not react with the resulting compound (5-1) and compound (6-1). Further, as the dissociation reaction solvent, it is preferred to select one which can easily be separated at the time of purification. As a specific example of the dissociation reaction solvent, preferred is an inert solvent such as a perfluorotrialkylamine or a perfluoronaphthalene, or a chlorofluorocarbon, specifically a chlorotrifluoroethylene oligomer having a high boiling point (for example, tradename: FLON LUBE). The amount of the dissociation reaction solvent is preferably from 0.10 to 10 times by mass, to the compound (4).

Further, in a case where the dissociation reaction of an ester bond is carried out by reacting the compound (4-1) with a nucleophilic agent or an electrophilic agent in a liquid phase, such a reaction may be carried out in the presence or absence of the dissociation reaction solvent, and it is preferably carried out in the absence of any solvent. As the nucleophilic agent, F$^-$ is preferred, and particularly preferred is F$^-$ derived from an alkali metal fluoride. As the alkali metal fluoride, NaF, NaHF$_2$, KF or CsF may be used, and among them, NaF is particularly preferred from the viewpoint of the economical efficiency. It is particularly preferred to carry out the dissociation reaction of the ester bond in the absence of any medium, since the compound (4-1) itself serves as a solvent, and it is not required to separate a solvent from the reaction product.

Further, in a case where the dissociation reaction of the ester bond is carried out by using $F^-$ as a nucleophilic agent, $F^-$ will be nucleophilically added to the carbonyl group present in the ester bond in the compound (4-1), whereby $R^{BF}CF_2O^-$ will be detached, and the compound (5-1) will be formed. Further, $F^-$ will be detached from $R^{BF}CF_2O^-$ to form the compound (6-1). The detached $F^-$ will react with another molecule of the compound (4) in a similar manner. Accordingly, the nucleophilic agent initially employed for the reaction may be in a catalytic amount or in an excess amount. The amount of the nucleophilic agent such as $F^-$ is preferably from 1 to 500 mol %, more preferably from 1 to 100 mol %, particularly preferably from 5 to 50 mol %, based on the compound (4-1). The reaction temperature is preferably from −30° C. to the boiling point of the solvent or the compound (4-1), more preferably from −20° C. to 250° C. This method is also preferably carried out while conducting distillation by a reaction apparatus having a distillation column.

From the reaction product of the dissociation reaction of the ester bond of the compound (4-1), the compound (5-1) and/or the compound (6-1) will be obtained; from the reaction product of the dissociation reaction of the ester bond of the compound (4-10), the compound (5-10) and/or the compound (6-10) will be obtained; and from the reaction product of the dissociation reaction of the ester bond of the compound (4-11), the compound (5-11) and/or the compound (6-11) will be obtained.

$$FCO\text{—}R^{AF}\text{—}COF \quad (5\text{-}1)$$

$$R^{BF}\text{—}COF \quad (6\text{-}1)$$

$$FCO\text{—}R^{AF1}\text{—}COF \quad (5\text{-}10)$$

$$R^{BF1}COF \quad (6\text{-}10)$$

$$FCO\text{—}R^{AF2}\text{—}COF \quad (5\text{-}11)$$

$$R^2COF \quad (6\text{-}11).$$

The following compounds may be mentioned as specific examples of the compound (5-1).

$FCOCF_2CF_2COF$, $FCOCF(CF_3)OCF_2CF_2CF_2COF$, $FCOCF(CF_3)OCF_2CF_2CF_2CF_2COF$, $FCOCF_2OCF_2COF$, $FCOCF_2O(CF_2)_2OCF(CF_3)COF$.

The following compounds may be mentioned as specific examples of the compound (6-1).

$CF_3CF_2COF$, $CF_2ClCFClCF_2COF$, $CF_2ClCF_2CFClCOF$, $CF_3CF_2CF_2OCF(CF_3)COF$, $CF_2ClCFClCF_2CF_2OCF(CF_3)COF$, $CClF_2CF_2COF$, $CBrF_2CF_2COF$, $CF_2BrCF_2OCF(CF_3)COF$, $CF_2ClCFClCF_2CF(CF_3)OCF(CF_3)COF$, $CF_3CF_2CF_2OCF(CF_3)CF_2OCF(CF_3)COF$, $CF_3CF_2CF_2OCF_2CF_2COF$.

Among the compound (5) and/or the compound (6) obtainable by the method of the present invention, a compound (5-1) and/or a compound (6-1) having a partial structure of "$C^1F\text{—}C^2\text{—}COF$" at a molecular terminal, can be led to a fluororesin raw material by converting the molecular terminal to "$C^1\text{=}C^2$" (wherein 1 and 2 in $C^1$ and $C^2$ are numerals specifying the carbon atoms) by a known reaction (Methods of Organic Chemistry, 4, Vol. 10b, Part 1, p. 703, etc.). Such a compound is a compound useful as a precursor for a fluororesin raw material.

For example, in a case where the method of the present invention is applied to the following compound, a useful fluororesin raw material can be produced.

For example, a compound (1-12) and a compound (2-12) are reacted to obtain a compound (3-12). The compound (3-12) is fluorinated in a liquid phase to obtain a compound (4-12). Then, the ester bond of the compound (4-12) is subjected to a dissociation reaction to obtain a compound (5-12) and/or a compound (2-12).

| | |
|---|---|
| $HO(CH_2)_4OH$ | (1-12) |
| $FCOCF_2CF_3$ | (2-12), |
| $CF_3CF_2COO(CH_2)_4OCOCF_2CF_3$ | (3-12) |
| $CF_3CF_2COO(CF_2)_4OCOCF_2CF_3$ | (4-12) |
| $FCO(CF_2)_2COF$ | (5-12) |

The compound (5-12) can be led to a useful fluororesin raw material ($CF_2\text{=}CFO(CF_2)_3COOCH_3$) by the following route. Here, HFPO represents hexafluoropropylene oxide.

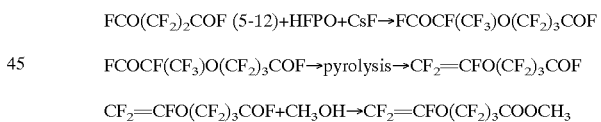

Further, a compound (1-13) and a compound (2-13) are reacted to obtain a compound (3-13) The compound (3-13) is fluorinated in a liquid phase to obtain a compound (4-13). Then, the ester bond of the compound (4-13) is subjected to a dissociation reaction to obtain a compound (5-13) and/or a compound (2-13). The compound (5-13) can also be led to a useful fluororesin raw material by the same route as mentioned above.

| | |
|---|---|
| $HOCH_2CH(CH_3)O(CH_2)_4OH$ | (1-13), |
| $FCOCF_2CF_3$ | (2-13), |
| $CF_3CF_2COOCH_2CH(CH_3)O(CH_2)_4OCOCF_2CF_3$ | (3-13), |
| $CF_3CF_2COOCF_2CF(CF_3)O(CF_2)_4OCOCF_2CF_3$ | (4-13), |
| $FCOCF(CF_3)O(CF_2)_3COF$ | (5-13), |

Further, a compound (1-14) and a compound (2-14) are reacted to obtain a compound (3-14). The compound (3-14)

is fluorinated in a liquid phase to obtain a compound (4-14). Then, the ester bond of the compound (4-14) is subjected to a dissociation reaction to obtain a compound (5-14) and/or a compound (2-14). The compound (5-14) is a compound present as a tautomer of lactone.

| | |
|---|---|
| $HO(CH_2)_2O(CH_2)_2OH$ | (1-14), |
| $FCOCF_2CF_3$ | (2-14), |
| $CF_3CF_2COO(CH_2)_2O(CH_2)_2OCOCF_2CF_3$ | (3-14), |
| $CF_3CF_2COO(CF_2)_2O(CF_2)_2OCOCF_2CF_3$ | (4-14), |
| $FCOCF_2OCF_2COF$ | (5-14). |

The following intermediate compounds in the above production routes are novel compounds useful as fluororesin raw materials.

| | |
|---|---|
| $CF_3CF_2COO(CH_2)_4OCOCF_2CF_3$ | (3-12), |
| $CF_3CF_2COOCH_2CH(CH_3)O(CH_2)_4OCOCF_2CF_3$ | (3-13), |
| $CF_3CF_2COO(CH_2)_2O(CH_2)_2OCOCF_2CF_3$ | (3-14), |
| $CF_3CF_2CF_2OCF(CF_3)COOCH_2CH(CH_3)O(CH_2)_5$—$OCOCF(CF_3)OCF_2CF_2CF_3$ | (3-15), |
| $CF_3CF_2COO(CH_2)_2O(CH_2)_2OCH(CH_3)CH_2OCOCF_2CF_3$ | (3-16), |
| $CF_3CF_2COOCF_2CF_2CF_2OCOCF_2CF_3$ | (4-12), |
| $CF_3CF_2COOCF_2CF(CF_3)OCF_2CF_2CF_2OCOCF_2CF_3$ | (4-13), |
| $CF_3CF_2COOCF_2CF_2OCF_2CF_2OCOCF_2CF_3$ | (4-14), |
| $CF_3CF_2CF_2OCF(CF_3)COOCF_2CF(CF_3)OCF_2(CF_2)_3$—$CF_2OCOCF(CF_3)OCF_2CF_2CF_3$ | (4-15), |
| $CF_3CF_2COO(CF_2)_2O(CF_2)_2OCF(CF_3)CF_2OCOCF_2CF_3$ | (4-16) |

Further, among compounds (5), the following compound (5-2) is a particularly useful compound wherein both terminals of the molecule can be converted to fluorinated vinyl groups.

$$FCO\text{-}Q^{F1}\text{-}R^{AF1}\text{-}Q^{F2}\text{-}COF \quad (5\text{-}2)$$

wherein $R^{AF}$: as defined above, and the preferred embodiments are also the same as mentioned above.

$Q^{F1}$, $Q^{F2}$: each represents or —$CF(CF_3)$— or —$CF_2CF_2$—.

The compound (5-2) is obtained together with the compound (6-1) from a reaction product, obtained by reacting a compound (1-2) and a compound (2-1) to obtain a compound (3-2), fluorinating the compound (3-2) in a liquid phase to obtain a compound (4-2) and subjecting the ester bond of the compound (4-2) to a dissociation reaction.

| | |
|---|---|
| $HOCH_2\text{-}Q^1\text{-}R^A\text{-}Q^2\text{-}CH_2OH$ | (1-2) |
| $XCOR^B$ | (2-1), |
| $R^BCOOCH_2\text{-}Q^1\text{-}R^A\text{-}Q^2\text{-}CH_2OCOR^B$ | (3-2) |
| $R^{BF}COOCF_2\text{-}Q^{F1}\text{-}R^{AF}\text{-}Q^{F2}\text{-}CF_2OCOR^{BF}$ | (4-2) |
| $FCO\text{-}Q^{F1}\text{-}R^{AF}\text{-}Q^{F2}\text{-}COF$ | (5-2) |
| $R^{BF}$—$COF$ | (6-1) | wherein $R^A$, $R^B$, $R^{AF}$, $R^{BF}$, X, $Q^{F1}$, $Q^{F2}$: as defined above.

$Q^1$, $Q^2$: they may be the same or different, and each represents —$CH(CH_3)$— or —$CH_2CH_2$—.

Further, the above $Q^1$ and $Q^2$ are preferably —$CH(CH_3)$—, and $Q^{F1}$ and $Q^{F2}$ are preferably —$CF(CF_3)$—.

In the method of the present invention, from the reaction product after the dissociation reaction of the ester bond, only the compound (5), only the compound (6), or both of the compounds (5) and (6), may be obtained. For example, in a case where the reaction of the present invention is carried out by using a compound (1-1) wherein $R^A$ is a bivalent organic group containing hydrogen atoms, and a compound (2-1) wherein $R^B$ is a perhalogenated monovalent organic group, a compound (5-1) wherein $R^A$ is fluorinated, can be obtained. Further, in a case where the reaction of the present invention is carried out by using a compound (1-1) wherein $R^A$ is a perhalogenated bivalent organic group and a compound (2-1) wherein $R^B$ is a monovalent organic group containing hydrogen atoms, a compound (6-1) having stoichiometrically two molecules fluorinated, will be obtained.

Further, in the method of the present invention, when the resulting compound (6) has the same structure as the compound (2), such a compound (6) is used as the compound (2), whereby the compound (5) can be continuously produced. For example, a method may be mentioned wherein a part or whole of the formed compound (6-1) is used as the compound (2-1) and reacted with the compound (1-1). In a case where such a method is carried out, it is preferred that the carbon number of $R^{BF}$ is adjusted to be at least 2, more preferably from 2 to 20, particularly preferably from 4 to 10.

The compound (5-2) obtained by the above method can be converted to a compound (7-2) by a pyrolysis.

$$CF_2\!\!=\!\!CF\text{—}R^{AF}\text{—}CF\!\!=\!\!CF_2 \quad (7\text{-}2)$$

Here, $R^{AF}$ is as defined above, and the preferred embodiments are also the same as mentioned above. The pyrolysis reaction can be carried out by a known method disclosed in e.g. J. Org. Chem., 34, 1841 (1969).

The following compounds may be mentioned as specific examples of the compound (7-2).

$$CF_2\!\!=\!\!CFO(CF_2)_2CF\!\!=\!\!CF_2,$$

$$CF_2\!\!=\!\!CFOCF_2CF\!\!=\!\!CF_2.$$

According to the method of the present invention, various fluorine-containing compounds may be produced by using a compound (1) and a compound (2) which are materials available inexpensively. Especially, by using the compound (1-1) and the compound (2-1) various diacyl fluoride compounds and a compound having a fluorinated vinyl groups at both terminals can be produced.

As the compound (1) and the compound (2) to be used as the raw materials in the method of the present invention, various compounds different in the structures of $R^A$ and $R^B$, are commercially sold and available inexpensively. And, according to the method of the present invention, from these raw material compounds, fluorine-containing compounds such as a diacyl fluoride compound and a compound having fluorinated vinyl groups at its both terminals, can be produced by a short process and in high yield. Further, by employing the method of the present invention, a low molecular weight fluorine-containing compound which used to be difficult to obtain by a conventional method, or a fluorine-containing compound having a complex structure, can easily be prepared. Further, the method of the present invention is not limited to the compounds disclosed as the above specific examples, and it is a method excellent in general applicability and applicable to various compounds, whereby a fluorine-containing compound having an optional skeleton can freely be produced. Further, by selecting the structures of $R^A$ and $R^B$, it is possible to carry out an efficient method wherein the product is re-used.

Further, according to the present invention, a novel intermediate which can be used as a raw material for a fluororesin, will be provided.

EXAMPLES

Now, the present invention will be described in further detail with reference to Examples. However, the present invention is by no means thereby restricted. In the following, gas chromatography is represented by GC, and the mass analysis of gas chromatography will be represented by GC-MS. Further, the purity determined by the peak area ratio of GC is represented by GC purity, and the purity obtained from the peak area ratio of the NMR spectrum, will be represented by NMR purity. For the quantitative analysis by $^{19}$F-NMR, perfluorobenzene was used as the internal standard sample. Further, tetramethylsilane was represented by TMS, and dichloropentafluoropropane is represented by R-225, and as R-225, AK225, tradename, manufactured by Asahi Glass Company, Limited, was used. Further, NMR spectrum data are shown within the apparent chemical shift range. The standard value for the standard substance $CDCl_3$ in $^{13}$C-NMR was set to be 76.9 ppm.

Example 1

Example 1-1

Preparation Example for $CF_3CF_2COO(CH_2)_4OCOCF_2CF_3$ $HO(CH_2)_4OH$ (200 g) was put into a flask and stirred while bubbling nitrogen gas. While maintaining the internal temperature from at 25 to 30° C., $FCOCF_2CF_3$ (800 g) was bubbled over a period of 2.5 hours. After completion of the dropwise addition, stirring was continued at room temperature for 15 hours, whereupon the crude liquid was recovered in a separating funnel. A $NaHCO_3$ saturated aqueous solution (500 ml) was added thereto at an internal temperature of at most 20° C. and neutralized twice. Further, the organic phase was washed three times with water (1 l), and the organic phase was recovered. After drying over magnesium sulfate, filtration was carried out to obtain a crude liquid.

The crude liquid was purified by silica gel column chromatography (developing solvent: R-225), and then, the crude liquid was concentrated by an evaporator, followed by distillation under reduced pressure, whereby 254.79 g of a fraction of 91 to 93° C./1.0 to 1.3 kPa (absolute pressure) was obtained. The GC purity was 99%. Further, the NMR spectrum of the fraction was measured to confirm that the main component was the above-identified compound.

NMR spectrum of the fraction:

$^1$H-NMR (300.4 MHz, solvent: $CDCl_3$, standard: TMS) δ (ppm): 1.85–1.89 (m, 4H), 4.41–4.45 (m, 4H).

$^{19}$F-NMR (282.65 MHz, solvent: $CDCl_3$, standard: $CFCl_3$) δ (ppm): −83.0 (6F), −121.4 (4F).

Example 1-2

Preparation Example for $CF_3CF_2COO(CF_2)_4OCOCF_2CF_3$

Into a 3000 ml autoclave made of nickel, R-113 (3232 g) was added, stirred and maintained at 25° C. At the gas outlet of the autoclave, a cooler maintained at −10° C. was installed. After supplying nitrogen gas for 1.5 hours, fluorine gas diluted to 20 vol % with nitrogen gas (hereinafter referred to as 20% fluorine gas) was supplied at 8.49 l/h for 2.3 hours.

Then, while supplying 20% fluorine gas at the same flow rate, a solution having $CF_3CF_2COO(CH_2)_4OCOCF_2CF_3$ (80 g) obtained in Example 1-1 dissolved in R-113 (800 g), was injected over a period of 45.7 hours. Further, 20% fluorine gas was supplied at the same flow rate for 0.5 hour, and further nitrogen gas was supplied for 3.0 hours. The formed product contained the above-identified compound as the main product, and the $^{19}$F-NMR yield was 92%.

$^{19}$F-NMR (376.0 MHz, solvent $CDCl_3$, standard: $CFCl_3$) δ (ppm): −83.8 (6F), −87.3 (4F), −122.6 (4F), −126.6 (4F).

Example 1-3

Preparation Example for $FCOCF_2CF_2COF$ by a Dissociation Reaction of an Ester Bond in Liquid Phase $CF_3CF_2COO(CF_2)_4OCOCF_2CF_3$ (5.0 g) obtained in Example 1-2 was charged together with 0.4 g of NaF powder into a flask and heated at 100° C. for 0.25 hour in an oil bath while vigorously stirring. At an upper portion of the flask, a container for gas recovery was installed. After cooling, 3.46 g of a gaseous sample was recovered. By the NMR spectrum, it was confirmed that $CF_3CF_2COF$ and the above-identified compound were the main components. The yield of the above-identified compound was 52.4%.

$^{19}$F-NMR (282.65 MHz solvent: $CDCl_3$, standard: $CFCl_3$) δ (ppm): 25.3 (2F), −118.2 (4F).

Example 2

Example 2-1

Preparation Example for $TsOCH(CH_3)CH_2OCH_2Ph$ (wherein Ts is a p-toluene Sulfonyl Group, and Ph is a Phenyl Group, and the Same Applies Hereinafter)

Into a four necked flask, $HOCH(CH_3)CH_2OCH_2Ph$ (50.0 g) was charged, and pyridine (150 ml) was added, followed by stirring. While cooling in an ice bath and maintaining the internal temperature at 5° C., p-toluene sulfonic acid chloride (63.1 g) was gradually added over a period of 1 hour. The mixture was added to water (165 ml), and dichloromethane (165 ml) was added for extraction, whereupon the liquids separated into two layers were separated. The organic layer was washed with $NaHCO_3$ (165 ml) and further washed three times with water (130 ml). It was dried over magnesium sulfate, filtered and then concentrated by an evaporator. Precipitated white crystals were collected by filtration and washed with hexane to obtain the above-identified compound (83.2 g).

$^1$H-NMR (300.4 MHz, solvent: $CDCl_3$, standard: TMS) δ (ppm): 1.31 (d, J=6.3 Hz, 3H), 2.40 (s, 3H), 3.46 (m, 2H), 4.41 (d, J=1.8 Hz, 2H), 4.73 (m, 1H), 7.19–7.34 (m, 7H), 7.75–7.89 (m, 2H).

Example 2-2

Preparation Example for $HO(CH_2)_4OCH(CH_3)CH_2OCH_2Ph$ $HO(CH_2)_4OH$ (37 g), potassium hydroxide (23 g) and dioxane (200 ml) were charged into a four necked flask and heated to an internal temperature of 102° C. to dissolve potassium hydroxide. A solution of TsOCH(CH$_3$)CH$_2$OCH$_2$Ph (63.7 g) obtained in Example 2-1 in dioxane (65 ml), was dropwise added over a period of 1 hour and stirred for 4 hours. The mixture was left to cool, then added to water (350 ml) and extracted three times with dichloromethane (100 ml). The organic layer was washed with water (20 ml). It was dried over magnesium sulfate, filtered and then concentrated by an evaporator to obtain a crude product (52 g). It was purified by silica gel column chromatography to obtain the above-identified compound (27.6 g).

$^1$H-NMR (300.4 MHz, solvent: CDCl$_3$, standard: TMS) δ (ppm): 1.15 (d, J=6.2 Hz, 3H), 1.64 (m, 4H), 2.98 (bs, 1H), 3.62–3.68 (m, 7H), 4.53 (d, J=2.35 Hz, 2H), 7.23–7.29 (m, 5H).

Example 2-3

Preparation Example for HO(CH$_2$)$_4$OCH(CH$_3$)CH$_2$OH

A round bottom flask was flushed with argon, and 5% palladium-carbon powder (1.5 g) was charged. Ethanol (100 ml) and HO(CH$_2$)$_4$OCH(CH$_3$)CH$_2$OCH$_2$Ph (15.2 g) obtained in Example 2-2 were added, then deaerated and flushed with nitrogen. The mixture was stirred at room temperature for 17 hours and then filtered through celite. The filtrate was concentrated by an evaporator to obtain the above-identified compound (8.65 g).

$^1$H-NMR (300.4 MHz, solvent: CDCl$_3$, standard: TMS) δ (ppm): 1.11 (q, J=6.2 Hz, 3H), 1.68 (m, 4H), 2.48 (bs, 2H), 3.41–3.68 (m, 7H).

Example 2-4

Preparation Example for CF$_3$CF$_2$COO(CH$_2$)$_4$OCH(CH$_3$)CH$_2$OCOCF$_2$CF$_3$ HO(CH$_2$)$_4$OCH(CH$_3$)CH$_2$OH (18.8 g) obtained in Example 2-3 was put into a round bottom flask and stirred while maintaining the internal temperature at 30° C. Together with nitrogen, CF$_3$CF$_2$COF (276 g) was supplied over 6 hours while maintaining the internal temperature at 30° C. After completion of the reaction, stirring was continued for 2 hours at an internal temperature of 30° C. while supplying nitrogen gas, whereupon a 5% NaHCO$_3$ aqueous solution (300 ml) was added at an internal temperature of at most 15° C.

The obtained crude liquid was subjected to liquid separation. The lower layer was washed twice with water (100 ml), dried over anhydrous magnesium sulfate and then filtered to obtain a crude liquid. The crude liquid was purified by silica gel column chromatography (developing solvent: R-225) to obtain the above-identified compound (25.9 g). The GC purity was 99%.

$^1$H-NMR (300.4 MHz, solvent: CDCl$_3$, standard: TMS) δ (ppm): 1.20 (d, J=6.3 Hz, 3H), 1.56~1.68 (m, 2H), 1.78~1.87 (m, 2H), 3.42~3.60 (m, 2H), 3.66~3.76 (m, 1H), 4.26~4.42 (m, 4H).

$^{19}$F-NMR (282.7 MHz, solvent: CDCCl$_3$, standard: CFCl$_3$) δ (ppm): −83.0 (3F), −83.0 (3F), −121.4 (2F), −121.5 (2F).

Example 2-5

Preparation Example for CF$_3$CF$_2$COO(CF$_2$)$_4$OCF(CF$_3$)CF$_2$OCOCF$_2$CF$_3$ Into a 500 ml autoclave made of nickel, R-113 (313 g) was charged, stirred and maintained at 25° C. At the gas outlet of the autoclave, a cooler maintained at 20° C., a packed layer of NaF pellets and a cooler maintained at −10° C. were installed in series. Further, a liquid returning line was installed to return a liquid condensed from the cooler maintained at −10° C. to the autoclave. After supplying nitrogen gas for 1.0 hour, 20% fluorine gas was supplied at a flow rate of 10.10 l/hr for 1.1 hours. Then, while supplying 20% fluorine gas at the same flow rate, a solution having CF$_3$CF$_2$COO(CH$_2$)$_4$OCH(CH$_3$)CH$_2$OCOCF$_2$CF$_3$ (4.95 g) obtained in Example 2-4 dissolved in R-113 (100 g), was injected over a period of 5.5 hours.

Then, while supplying 20% fluorine gas at the same flow rate, the temperature within the reactor was raised from 25° C. to 40° C., and at the same time, a R-113 solution (9 ml) containing 0.01 g/ml of benzene, was injected. The injection inlet for benzene and the outlet valve of the autoclave were closed, and when the pressure became 0.20 MPa (gauge pressure), the fluorine gas inlet valve of the autoclave was closed. Further, stirring was continued for 0.4 hour. Then, the pressure in the reactor was returned to normal pressure, and while maintaining the temperature at 40° C., the above-mentioned benzene solution (6 ml) was injected. The operation of closing the benzene injection inlet and the outlet valve of the autoclave and, when the pressure became 0.20 MPa (gauge pressure) closing the fluorine gas inlet valve of the autoclave, followed by stirring for 0.4 hour, was repeated four times.

The total amount of benzene injected was 0.336 g, and the total amount of R-113 injected was 33 ml. Further, nitrogen gas was supplied for 1.5 hours. The $^{19}$F-NMR yield of the above-identified compound contained in the product, was 94%.

$^{19}$F-NMR (376.0 MHz, solvent CDCl$_3$, standard: CFCl$_3$) δ (ppm): −80.4 (3F), −81.0 (2F), −83.3 (3F), −83.4 (3F), −86.8 (2F), −86.9 (2F), −122.1 (4F), −125.9 (2F), −126.2 (2F), −145.6 (1F).

Example 2-6

Preparation Example for FCOCF(CF$_3$)O(CF$_2$)$_3$COF by a Dissociation Reaction of an Ester Bond in a Liquid Phase CF$_3$CF$_2$COO(CF$_2$)$_4$OCF(CF$_3$)CF$_2$OCOCF$_2$CF$_3$ (0.6 g) obtained in Example 2-5 was charged together with NaF powder (0.008 g) into a flask and heated at 100° C. for 5.66 hours in an oil bath, while vigorously stirring. At an upper portion of the flask, a liquid sample (0.65 g) was recovered through a reflux condenser having the temperature adjusted to 90° C. From the NMR spectrum, it was confirmed that the above-identified compound was the main component. The yield was 77.1%.

$^{19}$F-NMR (376 MHz, solvent: CDCl$_3$, standard: CFCl$_3$) δ (ppm): 26.5 (1F), 25.0 (1F), −78.3~−78.8 (1F), −82.1 (3F), −86.0~−86.4 (1F), −118.5 (2F), −126.6 (2F), −131.0 (1F).

Example 3

Example 3-1

Preparation Example for HOCH$_2$CH(CH$_3$)O(CH$_2$)$_5$OH

CH$_3$CH(OH)CH$_2$OCH$_2$Ph (50.0 g) and pyridine (150 ml) were put into a flask, and under cooling with ice, p-toluenesulfonic acid chloride (63.2 g) was added over a period of 30 minutes. The mixture was stirred at room temperature for 4 days, and then water (150 ml) was added, followed by extraction twice with dichloromethane (100 ml). The extracted organic phase was washed twice with a KHCO$_3$ saturated aqueous solution (100 ml) and twice with water (100 ml), dried over magnesium sulfate, filtered and further concentrated to obtain PhCH$_2$OCH$_2$CH(CH$_3$)OTs (71.2 g).

Into another flask, KOH (25.8 g), HO(CH$_2$)$_5$OH (47.9 g) and dioxane (200 ml) were charged and stirred at 90° C. until KOH was dissolved. Then, from a dropping funnel, PhCH$_2$OCH$_2$CH(CH$_3$)OTs (71.2 g) and dioxane (75 ml) were added at 90° C. over a period of 20 minutes. After further stirring at 80° C. for 20 hours, water (350 ml) was added. Extraction with dichloromethane (100 ml) was carried out three times, and the extracted organic phase was washed with water (150 ml), then dried over anhydrous magnesium sulfate, filtered and further concentrated. The concentrated liquid was purified by silica gel column (eluent: hexane/ethyl acetate) to obtain PhCH$_2$OCH$_2$CH(CH$_3$)O(CH$_2$)$_5$OH (20.8 g).

Into a flask, 5% palladium-carbon powder (4 g) and ethanol (200 ml) were charged, and nitrogen was supplied for 1 hour. The interior was vacuumed and flushed with hydrogen, whereupon PhCH$_2$OCH$_2$CH(CH$_3$)O(CH$_2$)$_5$OH (18 ml) was added by a syringe and stirred for 24 hours. The crude liquid was filtered and concentrated to obtain the above-identified compound (11.9 g).

Example 3-2

Preparation Example for CF$_3$CF$_2$CF$_2$OCF(CF$_3$)COOCH$_2$CH(CH$_3$)O(CH$_2$)$_5$OCOCF(CF$_3$)OCF$_2$CF$_2$CF$_3$ HOCH$_2$CH(CH$_3$)O(CH$_2$)$_5$OH (11.8 g) obtained in Example 3-1 was put into a flask, and as a HF scavenger, ethylamine (30.3 g) was added and stirred. While maintaining the internal temperature to a level of at most 15° C., CF$_3$CF$_2$CF$_2$OCF(CF$_3$)COF (49.8 g) was dropwise added over a period of 1 hour. After completion of the dropwise addition, the mixture was stirred at room temperature for 2 hours, and excess CF$_3$CF$_2$CF$_2$OCF(CF$_3$)COF was distilled off under reduced pressure. The product was washed with water (50 ml) and then washed three times with a 0.1N hydrochloric acid aqueous solution (30 ml) to remove the remaining triethylamine. Further, the organic layer was washed three times with a KHCO$_3$ saturated aqueous solution (30 ml), dried over magnesium sulfate and then filtered to obtain a liquid (53.0 g) having a GC purity of 97%.

The NMR spectrum was measured, and it was confirmed that the main component was the above-identified compound and a mixture of diastereomers.

$^1$H-NMR (300.4 MHz, solvent CDCl$_3$, standard: TMS) δ (ppm): 1.19 (d, J=6.3 Hz, 3H), 1.39–1.49 (m, 2H), 1.54–1.63 (m, 2H), 1.71–1.80 (m, 2H), 3.39–3.53 (m, 2H), 3.66–3.72 (m, 1H), 4.21–4.46 (m, 4H).

$^{19}$F-NMR (282.7 MHz solvent CDCl$_3$, standard: CFCl$_3$) δ (ppm): –80.9 (2F), –82.3 (6F), –83.1 (6F), –87.4 (2F), –130.7 (4F), –132.7 (2F).

Example 3-3

Preparation Example for CF$_3$(CF$_2$)$_2$OCF(CF$_3$)COOCF$_2$C(CF$_3$)O(CF$_2$)$_5$OCOCF(CF$_3$)OCF$_2$CF$_2$CF$_3$ Into a 500 ml autoclave made of nickel, R-113 (312.2 g) was added and stirred, and the internal temperature was adjusted to 25° C. At the gas outlet of the autoclave, a cooler maintained at 25° C., a packed layer of NaF pellets and a cooler maintained at –8° C., were installed in series. Further, a liquid returning line was installed in order to return a liquid condensed from the cooler maintained at –8° C. to the autoclave. After supplying nitrogen gas for 1 hour, 20% fluorine gas was supplied at a flow rate of 11.0 l/hr for 1 hour, and while supplying at the same flow rate, a R-113 (200 g) solution of the liquid product (10 g) obtained in Example 3-2, was injected over a period of 6 hours.

Then, the internal temperature was raised to 40° C., and while supplying 20% fluorine gas at the above-mentioned flow rate, a R-113 solution of benzene (0.01 g/ml) was injected. The outlet valve of the autoclave was closed, and when the pressure became 0.20 MPa (gauge pressure), the inlet valve of the autoclave was closed, and stirring was continued for 20 minutes. Further, the same operation was repeated five times. During this period, benzene was supplied in a total amount of 0.27 g, and R-113 was supplied in a total amount of 42.1 g. Thereafter, nitrogen gas was supplied for 1 hour, and the reaction mixture was taken out by decantation. The obtained crude liquid was concentrated by an evaporator and quantified, whereby the $^{19}$F-NMR yield was 70%. The crude liquid was distilled under reduced pressure to obtain the above-identified compound. The product was a mixture of diastereomers.

$^{19}$F-NMR (282.7 MHz, solvent CDCl$_3$/C$_6$F$_6$, standard: CFCl$_3$) δ (ppm): –79.2~–80.7 (7F), –81.5~–82.0 (12F), –85.9~–87 (6F), –122.4 (2F), –125.3 (4F), –129.6 (4F), –131.4 (2F), –144.9 (1F).

Example 3-3

Preparation Example for FCOCF(CF$_3$)O(CF$_2$)$_4$COF

The product (5 g) obtained in Example 3-2 was charged into a 30 ml flask equipped with a reflux condenser of 80° C., and potassium fluoride (0.06 g) was added, whereupon while stirring under heating at 150° C., the formed gas was cooled to –78° C. and recovered in a glass trap. When the reaction proceeded, and the liquid in the flask was all disappeared, the reaction was terminated. In the glass trap, 4.8 g of the product was obtained.

As a result of the GC analysis, it was confirmed that CF$_3$CF$_2$CF$_2$OCF(CF$_3$)COF and FCOCF(CF$_3$)O(CF$_2$)$_4$COF were formed in a ratio of 2:1 (molar ratio).

Example 3-4

Preparation Example for CF$_2$=CFOCF$_2$CF$_2$CF=CF$_2$ by Pyrolysis

In the same manner as the method disclosed in J. Org. Chem., 34, 1841 (1969), pyrolysis was carried out by using FCOCF(CF$_3$)O(CF$_2$)$_4$COF obtained by the reaction of Example 3-3, and formation of the above-identified compound was confirmed by GC.

Example 4

Example 4-1

Preparation Example for CF$_3$CF$_2$COO(CH$_2$)$_2$O(CH$_2$)$_2$OCOCF$_2$CF$_3$ by an Esterification Reaction HO(CH$_2$)$_2$O(CH$_2$)$_2$OH (40 g) was put into a flask and stirred while maintaining the internal temperature at 30° C. While maintaining the internal temperature of the flask at 30° C., nitrogen and CF$_3$CF$_2$COF (388 g) were supplied over a period of 1.5 hours. After completion of the reaction, while supplying nitrogen gas, stirring was continued at an internal temperature of 30° C. for 2 hours, and then the internal temperature of the flask was brought to at most 15° C., whereupon 5% NaHCO$_3$ (300 ml) was added.

The obtained crude liquid was subjected to liquid separation, and the lower layer was washed twice with 100 ml of water, dried over magnesium sulfate and then filtered to obtain a crude liquid. By distillation under reduced pressure, the above-identified compound (91.8 g) was obtained as a fraction of 81 to 84° C./1.3 kPa (absolute pressure). The GC purity was 99%.

$^1$H-NMR (300.4 MHz, solvent: CDCl$_3$, standard: TMS) δ (ppm): 3.77–3.80 (m, 4H), 4.50–4.53 (m, 4H).

$^{19}$F-NMR (282.7 MHz solvent: CDCl$_3$, standard: CFCl$_3$) δ (ppm): −83.0 (6F), −121.6 (4F).

Example 4-2

Preparation Example for CF$_3$CF$_2$COO(CF$_2$)$_2$O-(CF$_2$)$_2$OCOCF$_2$CF$_3$ by a Fluorination Reaction In the same autoclave as in Example 2-5, R-113 (312 g) was added, and preparation was made under the same condition except that 20% fluorine gas was supplied at a flow rate of 9.47 l/hr for 1 hour. Then, while supplying 20% fluorine gas at the same flow rate, a solution having CF$_3$CF$_2$COO(CH$_2$)$_2$O(CH$_2$)$_2$OCOCF$_2$CF$_3$ (7.0 g) obtained in Example 4-1 dissolved in R-113 (140 g), was injected over a period of 4.9 hours.

Then, while supplying 20% fluorine gas at the same flow rate and maintaining the pressure of the reactor at 0.15 MPa (gauge pressure), a R-113 solution (9 ml) containing 0.01 g/ml of benzene, was injected while raising the temperature from 25° C. to 40° C., and the benzene injection inlet of the autoclave was closed, and stirring was continued for 0.3 hour. Then, while maintaining the pressure in the reactor at 0.15 MPa (gauge pressure) and the temperature at 40° C., the above benzene solution (6 ml) was injected and stirred for 0.3 hour. Further, while maintaining the temperature in the reactor at 40° C., the above benzene solution (6 ml) was injected and stirred for 1.1 hours, and nitrogen gas was supplied for 1.0 hour. The $^{19}$F-NMR yield of the above-identified compound contained in the product was 94%.

$^{19}$F-NMR (376.0 MHz solvent CDCl$_3$, standard: CFCl$_3$) δ (ppm): −83.4 (6F), −88.8 (4F), −92.2 (4F), −122.2 (4F).

Example 4-3

Preparation Example for FCOCF$_2$OCF$_2$COF by Dissociation of an Ester Bond in a Liquid Phase CF$_3$CF$_2$COO(CF$_2$)$_2$O(CF$_2$)$_2$OCOCF$_2$CF$_3$ (6.0 g) obtained in Example 4-2 was charged together with NaF (0.09 g) powder into a flask and heated at 100° C. for 5 hours in an oil bath, while vigorously stirring. At the upper portion of the flask, a reflux condenser adjusted to a temperature of 20° C. and a gas-collecting fluororesin container were installed in series. After cooling, 0.5 g of a liquid sample and 5.4 g of a gaseous sample were recovered. As a result of the analysis by GC-MS, it was confirmed that the gaseous sample contained CF$_3$CF$_2$COF and the above-identified compound as the main products. The yield of the above-identified compound was obtained and found to be 85.6%.

Example 5

Example 5-1

Preparation Example for HO(CH$_2$)$_2$O(CH$_2$)$_2$OCH(CH$_3$)CH$_2$OCH$_2$Ph

HO(CH$_2$)$_2$O(CH$_2$)$_2$OH (21.2 g), potassium hydroxide (11.2 g) and dioxane (100 ml) were charged into a four necked flask and heated to an internal temperature of 63° C. to dissolve potassium hydroxide. A solution obtained by dissolving 32.0 g of TsOCH(CH$_3$)CH$_2$OCH$_2$Ph obtained in Example 2-1 in dioxane (50 ml), was dropwise added over a period of 30 minutes, and while maintaining the internal temperature within a range of from 60 to 100° C., stirring was continued for 13.5 hours. The mixture was left to cool, then added to water (200 ml) and extracted three times with dichloromethane (50 ml). The organic layer was washed with water (20 ml). It was dried over magnesium sulfate, filtered and then concentrated by an evaporator to obtain a crude product (52 g). it was purified by silica gel chromatography to obtain 9.32 g of the above-identified compound.

$^1$H-NMR (300.4 MHz, solvent: CDCl$_3$, standard: TMS) δ (ppm): 1.17 (d, J=6.3 Hz, 3H), 2.8 (bs, 1H), 3.40–3.52 (m, 2H), 3.58–3.73 (m, 7H), 4.54 (m, 2H), 7.26–7.34 (m, 5H).

Example 5-2

Preparation Example for HO(CH$_2$)$_2$O(CH$_2$)$_2$OCH(CH$_3$)CH$_2$OH

Interior of a round bottom flask was flushed with argon, and 5% palladium-carbon powder (0.9 g) was charged. Ethanol (50 ml) and HO(CH$_2$)$_2$O(CH$_2$)$_2$OCH(CH$_3$)CH$_2$OCH$_2$Ph (9.21 g) obtained in Example 5-1 were added, then deaerated and flushed with hydrogen. The mixture was stirred at room temperature for 17 hours and then filtered through celite. The filtrate was concentrated by an evaporator to obtain 5.45 g of the above-identified compound.

$^1$H-NMR (300.4 MHz, solvent: CDCl$_3$, solvent: TMS) δ (ppm): 1.13 (d, J=6.2 Hz, 3H), 3.20–3.82 (m, 11H).

Example 5-3

Preparation Example for CF$_3$CF$_2$COO(CH$_2$)$_2$O(CH$_2$)$_2$OCH(CH$_3$)CH$_2$OCOCF$_2$CF$_3$ HO(CH$_2$)$_2$O(CH$_2$)$_2$OCH(CH$_3$)CH$_2$OH (5.1 g) obtained in Example 5-2 and chloroform (10 g) were charged into a flask and stirred while maintaining the internal temperature at 30° C. Together with nitrogen, CF$_3$CF$_2$COF (191 g) was supplied while maintaining the internal temperature at 30° C. After completion of the reaction, while supplying nitrogen gas, stirring was continued at an internal temperature of 30° C. for 2 hours, and then, a 5% NaHCO$_3$ aqueous solution (30 ml) was added at an internal temperature of at most 15° C.

The obtained crude liquid was subjected to liquid separation and purified by silica gel column chromatography (developing solvent: R-225) to obtain the above-identified compound (5.0 g). The GC purity was 99%.

$^1$H-NMR (300.4 MHz, solvent: CDCl$_3$, standard: TMS) δ (ppm): 1.21 (d, J=6.6 Hz, 3H), 3.58–3.81 (m, 7H), 4.33 (d, J=5.4 Hz, 2H), 4.50–4.53 (m, 2H).

$^{19}$F-NMR (282.7 MHz, solvent: CDCl$_3$, standard: CFCl$_3$) δ (ppm): −82.96 (3F), −82.99 (3F), −121.46 (2F), −121.53 (2F).

Example 5-4

Preparation Example for CF$_3$CF$_2$COO(CF$_2$)$_2$O-(CF$_2$)$_2$OCF(CF$_3$)CF$_2$OCOCF$_2$CF$_3$ In the same autoclave as in Example 2-5, R-113 (312 g) was added, and preparation was made under the same conditions except that 20% fluorine gas was supplied at a flow rate of 12.72 l/hr for 1 hour.

Then, while supplying 20% fluorine gas at the same flow rate, a solution having CF$_3$CF$_2$COO(CH$_2$)$_2$O(CH$_2$)$_2$OCH(CH$_3$)CH$_2$OCOCF$_2$CF$_3$ (5.0 g) obtained in Example 5-3 dissolved in R-113 (100 g), was injected over a period of 3.9 hours.

Then, while supplying 20% fluorine gas at the same flow rate and maintaining the pressure of the reactor at 0.15 MPa (gauge pressure), the temperature was raised from 25° C. to 40° C., and at the same time, a R-113 solution (9 ml) containing 0.01 g/ml of benzene, was injected. The benzene injection inlet of the autoclave was closed, and stirring was continued for 0.3 hour. Then, while maintaining the pressure of the reactor at 0.15 MPa (gauge pressure) and the temperature at 40° C., the above benzene solution (6 ml) was injected, and stirring was continued for 0.3 hour. Further, the operation of injecting the benzene solution (6 ml) and stirring for 0.3 hour, was repeated four times under the same conditions, whereupon stirring was carried out for 0.7 hour. Further, nitrogen gas was supplied for 1.0 hour. The $^{19}$F-NMR yield of the above-identified compound contained in the product, was 89%.

$^{19}$F-NMR (376.0 MHz, solvent CDCl$_3$, standard: CFCl$_3$) δ (ppm): −80.5 (3F), −83.4 (6F), −85.9∼87.5 (4F), −89.0 (4F), −92.3 (2F), −122.3 (4F), −145.6 (1F).

Example 5-5

Preparation Example for FCOCF$_2$O(CF$_2$)$_2$OCF(CF$_3$)COF

CF$_3$CF$_2$COO(CF$_2$)$_2$O(CF$_2$)$_2$OCF(CF$_3$)CF$_2$OCOCF$_2$CF$_3$ (5.1 g) obtained in Example 5-4 was charged together with 0.09 g of KF powder into a flask and heated at 40° C. for 2 hours in an oil bath while vigorously stirring. At an upper portion of the flask, a reflux condenser adjusted to a temperature of 20° C. and a gas-collecting fluororesin container were installed in series. After cooling, a liquid sample (3.2 g) and a gaseous sample (1.6 g) were recovered. By GC-MS, it was confirmed that the gaseous sample contained CF$_3$CF$_2$COF as the main product, and the liquid sample contained the above-identified compound as the main product. Further, the $^{19}$F-NMR yield of the above-identified compound contained in the product was 92%.

$^{19}$F-NMR (376.0 MHz, solvent CDCl$_3$, standard: CFCl$_3$) δ (ppm): 26.7 (1F), 14.6 (1F), −77.2 (2F), −82.0 (3F), −84.2 (1F) −88.2 (2F), −91.3 (1F), −131.0 (1F).

Example 6

Preparation Example for FCO(CF$_2$)$_2$COF

Into a 3000 ml autoclave made of nickel, R-113 (2767 g) was added, stirred and maintained at 25° C. At the gas outlet of the autoclave, a cooler maintained at 20° C., a packed layer of NaF pellets and a cooler maintained at −10° C. were installed in series. Further, a liquid returning line was installed in order to return a liquid condensed from the cooler maintained at −10° C. to the autoclave. After supplying nitrogen gas for 2.3 hours, fluorine gas diluted to 50% with nitrogen gas (hereinafter referred to as 50% fluorine gas) was supplied at a flow rate of 7.79 l/hr for 3 hours. Then, while supplying 50% fluorine gas at the same flow rate, as the first fluorination, a R-113 (250.2 g) solution of CF$_3$CF$_2$COO(CH$_2$)$_4$OCOCF$_2$CF$_3$ (25.0 g) obtained in Example 1-1, was injected over a period of 6.0 hours, and the reaction crude liquid (241.1 g, $^{19}$F-NMR yield: 51%) was withdrawn. Second fluorination was carried out in the same manner as the first fluorination, and the reaction crude liquid (241.0 g, $^{19}$F-NMR yield: 83%) was withdrawn. Then, third fluorination was carried out in the same manner as the first fluorination, and the reaction crude liquid (240.9 g, $^{19}$F-NMR yield: 89%) was withdrawn. Further, nitrogen gas was supplied for 1.8 hours, and the reaction crude liquid (2804.4 g, $^{19}$F-NMR yield of the above-identified compound: 86%) was withdrawn.

Using the obtained above-identified compound, the reaction was carried out in the same manner as in Example 1-3 to obtain FCO(CF$_2$)$_2$COF.

Industrial Applicability

According to the method of the present invention, a compound useful as a raw material for the production of various fluororesins can be obtained in high yield in a short process by using an inexpensive readily-available starting material. Further, according to the present invention, a novel compound useful as the raw material for producing fluororesins will be provided. The method of the present invention is a method excellent in general applicability, which can be applied to the production of various compounds by using a starting material which is readily available. And, by applying the method of the present invention, it is possible to produce known compounds economically advantageously, and it is possible to provide various novel fluorine-containing compounds.

The entire disclosures of Japanese Patent Application No. 2000-210184 filed on Jul. 11, 2000, Japanese Patent Application No. 2000-294994 filed on Sep. 27, 2000 and Japanese Patent Application No. 2001-107560 filed on Apr. 5, 2001 including specifications, claims and summaries are incorporated herein by reference in their entireties.

What is claimed is:

1. A method for producing a fluorine-containing compound, which comprises reacting the following compound (1) with the following compound (2) to produce the following compound (3) (provided that the compound (3) is a compound having a fluorine content of at least 30 mass % and has a hydrogen atom or an unsaturated bond which can be fluorinated), fluorinating the compound (3) in a liquid phase to produce the following compound (4), followed by a cleavage reaction of E$^F$ of the compound (4) to obtain a compound (5) and/or a compound (6):

$$E^1\text{-}R^A\text{-}E^1 \quad (1)$$

$$E^2\text{-}R^B \quad (2)$$

$$R^B\text{-}E\text{-}R^A\text{-}E\text{-}R^B \quad (3)$$

$$R^{BF}\text{-}E^F\text{-}R^{AF}\text{-}E^F\text{-}R^{BF} \quad (4)$$

$$E^{F1}\text{-}R^{AF}\text{-}E^{F1} \quad (5)$$

$$R^{BF}\text{-}E^{F2} \quad (6)$$

wherein $R^A$, $R^B$: $R^A$ is a fluorine-containing bivalent organic group which is the same as $R^{AF}$, or a bivalent organic group which will be converted to $R^{AF}$ by a fluorination reaction, and $R^B$ is a monovalent organic group which is the same as $R^{BF}$, or a monovalent organic group which will be converted to $R^{BF}$ by a fluorination reaction, $R^{AF}$, $R^{BF}$: $R^{AF}$ is a fluorine-containing bivalent organic group which is the same as or different from $R^A$, and when different, it is a group having $R^A$ fluorinated, and $R^{BF}$ is a fluorine-containing monovalent organic group which is the same as or different from $R^B$, and when different, it is a group having $R^B$ fluorinated, $E^1$, $E^2$: reactive groups which will react to each other to form a bivalent connecting group (E), E: a bivalent connecting group formed by the reaction of $E^1$ and $E^2$, $E^F$: a group which is the same as E, or a group having E fluorinated, provided that at least one selected from $R^{AF}$, $R^{BF}$ and $E^F$, is a group formed by a fluorination reaction, and $E^{F1}$, $E^{F2}$: each independently is a group formed by cleavage of $E^F$.

2. The method according to claim 1, wherein the compound (1) is the following compound (1-1), the compound (2) is the following compound (2-1), the compound (3) is the following compound (3-1), the compound (4) is the following compound (4-1), the cleavage reaction of $E^F$ is a reaction to cleave the ester bond of the compound (4-1), the compound (5) is the following compound (5-1), and the compound (6) is the following compound (6-1):

$$HOCH_2\text{—}R^A\text{—}CH_2OH \qquad (1\text{-}1)$$

$$XCOR^B \qquad (2\text{-}1)$$

$$R^BCOOCH_2\text{—}R^A\text{—}CH_2OCOR^B \qquad (3\text{-}1)$$

$$R^{BF}COOCF_2\text{—}R^{AF}\text{—}CF_2OCOR^{BF} \qquad (4\text{-}1)$$

$$FCO\text{—}R^{AF}\text{—}COF \qquad (5\text{-}1)$$

$$R^{BF}\text{—}COF \qquad (6\text{-}1)$$

wherein $R^A$, $R^B$, $R^{AF}$ and $R^{BF}$: as defined above, and

X: a halogen atom.

3. The method according to claim 2, which further comprises reacting compound (6-1) with compound (1-1) to obtain compound (3-1).

4. The method according to claim 1, wherein the compound (1) is the following compound (1-2), the compound (2) is the following compound (2-1), the compound (3) is the following compound (3-2), the compound (4) is the following compound (4-2), the cleavage reaction of $E^F$ is a reaction to cleave the ester bond of the compound (4-2), the compound (5) is the following compound (5-2), and the compound (6) is the following compound (6-1):

$$HOCH_2\text{-}Q^1\text{-}R^A\text{-}Q^2\text{-}CH_2OH \qquad (1\text{-}2)$$

$$XCOR^B \qquad (2\text{-}1)$$

$$R^BCOOCH_2\text{-}Q^1\text{-}R^A\text{-}Q^2\text{-}CH_2OCOR^B \qquad (3\text{-}2)$$

$$R^{BF}COOCF_2\text{-}Q^{F1}\text{-}R^{AF}\text{-}Q^{F2}\text{-}CF_2OCOR^{BF} \qquad (4\text{-}2)$$

$$FCO\text{-}Q^{F1}\text{-}R^{AF}\text{-}Q^{F2}\text{-}COF \qquad (5\text{-}2)$$

$$R^{BF}\text{—}COF \qquad (6\text{-}1)$$

wherein $R^A$, $R^B$, $R^{AF}$ and $R^{BF}$: as defined above,

X: a halogen atom, $Q^1$, $Q^2$: they may be the same or different, and each represents —CH(CH$_3$)— or —CH$_2$CH$_2$—, and $Q^{F1}$, $Q^{F2}$: $Q^{F1}$ is a group which corresponds to $Q^1$, and $Q^{F2}$ is a group which corresponds to $Q^2$, and each represents —CF(CF$_3$)— or —CF$_2$CF$_2$—.

5. The method according to claim 4, wherein the compound (5-2) is pyrolyzed to produce the following compound (7-2):

$$CF_2\text{=}CF\text{—}R^{AF}\text{—}CF\text{=}CF_2 \qquad (7\text{-}2)$$

wherein $R^{AF}$ is as defined above.

6. The method according to claim 1, wherein the carbon number of $R^{BF}$ is from 2 to 20.

7. The method according to claim 1, wherein the compound (1) has a fluorine content of 0 mass % and a molecular weight of not more than 200, and the compound (3) has a fluorine content of from 30 to 76 mass % and a molecular weight of more than 200 and not more than 1,000.

8. The method according to claim 1, wherein the fluorination in the liquid phase is carried out by fluorination with fluorine in a solvent.

9. The method according to claim 1, wherein compound (1) is selected from the group consisting of HO(CH$_2$)$_n$OH, HO(CH$_2$CH(CH$_3$)O)$_m$(CH$_2$)$_p$OH, and HO(CH$_2$CH$_2$O)$_k$(CH$_2$)$_r$OH;

wherein n ranges from 4 to 10, m ranges from 1 to 10, p ranges from 3 to 5, k ranges from 1 to 10, and r ranges from 3 to 5.

10. The method according to claim 1, wherein the liquid phase comprises a solvent present in an amount that ranges from 10 to 100 times by mass based on the amount of compound (3).

11. The method according to claim 1, wherein the liquid phase comprises fluorine (F$_2$) and the mole ratio of F$_2$ to compound (3) is at least 1.1.

12. The method according to claim 1, wherein the liquid phase comprises fluorine (F$_2$) and the mole ratio of F$_2$ to compound (3) is at least 1.5.

13. The method according to claim 1, wherein said fluorinating occurs at a temperature that ranges from –50° C. to +100° C.

14. The method according to claim 1, wherein said fluorinating occurs at a temperature that ranges from –20° C. to +50° C.

15. The method according to claim 1, wherein the liquid phase comprises an organic hydrocarbon.

16. The method according to claim 1, wherein the cleavage reaction occurs by reacting compound (4-1) with a nucleophilic agent or an electrophilic agent in a liquid phase.

17. The method according to claim 1, wherein the cleavage reaction occurs by reacting compound (4-1) with a nucleophilic agent or an electrophilic agent in the absence of solvent.

18. The method according to claim 2, wherein the cleavage reaction occurs by reacting compound (4-1) with a nucleophilic agent in the absence of solvent.

19. The method according to claim 18, wherein the nucleophilic agent is selected from the group consisting of NaF, NaHF$_2$, KF, CsF, and mixtures thereof.

20. The method according to claim 18, wherein the nucleophilic agent is NaF.

21. The method according to claim 1, wherein the molecular weight of the compound of the formula (3) is from 200 to 1,000.

22. The method according to claim 1, wherein the carbon number of $R^B$ is from 2 to 10.

23. The method according to claim 1, wherein the carbon number of $R^B$ is from 4 to 10.

* * * * *